US010563233B2

(12) United States Patent
Kavazanjian et al.

(10) Patent No.: US 10,563,233 B2
(45) Date of Patent: Feb. 18, 2020

(54) CEMENTATION METHODS

(71) Applicant: Arizona Board of Regents on behalf of Arizona State University, Scottsdale, AZ (US)

(72) Inventors: Edward Kavazanjian, Tempe, AZ (US); Nasser Hamdan, Scottsdale, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 15/803,700

(22) Filed: Nov. 3, 2017

(65) Prior Publication Data

US 2018/0119185 A1 May 3, 2018

Related U.S. Application Data

(63) Continuation-in-part of application No. 13/944,450, filed on Jul. 17, 2013, now abandoned.

(60) Provisional application No. 61/672,597, filed on Jul. 17, 2012.

(51) Int. Cl.
| | |
|---|---|
| *C12P 9/00* | (2006.01) |
| *C12N 9/80* | (2006.01) |
| *C12P 3/00* | (2006.01) |
| *C01F 11/00* | (2006.01) |
| *C04B 28/10* | (2006.01) |
| *C04B 103/00* | (2006.01) |
| *C04B 111/72* | (2006.01) |

(52) U.S. Cl.
CPC ............. *C12P 9/00* (2013.01); *C01F 11/00* (2013.01); *C04B 28/10* (2013.01); *C12N 9/80* (2013.01); *C12P 3/00* (2013.01); *C12Y 305/01005* (2013.01); *C04B 2103/0001* (2013.01); *C04B 2111/72* (2013.01)

(58) Field of Classification Search
None
See application file for complete search history.

(56) References Cited

U.S. PATENT DOCUMENTS

| | | | |
|---|---|---|---|
| 4,002,204 A | 1/1977 | Cavin et al. | |
| 6,401,819 B1 | 6/2002 | Harris et al. | |
| 7,841,804 B2 * | 11/2010 | Ostvold | ........ C09K 17/02 405/263 |
| 8,420,362 B2 | 4/2013 | Crawford et al. | |
| 2002/0156337 A1 | 10/2002 | Jensen et al. | |
| 2012/0308306 A1 | 12/2012 | Kruse et al. | |

OTHER PUBLICATIONS

Bang et al., "Application of Novel Biological Technique in Dust Suppression", TRB 2009 Annual Meeting (2009) ( Year: 2009).*

* cited by examiner

*Primary Examiner* — Jeffrey D Washville
(74) *Attorney, Agent, or Firm* — Snell & Wilmer L.L.P.

(57) ABSTRACT

The present invention provides methods for mineral precipitation and/or cementation of permeable or fractured non-porous materials using isolated urease.

15 Claims, 10 Drawing Sheets

Specification includes a Sequence Listing.

SEQUENCE LISTING

<160> NUMBER OF SEQ ID NOS: 6

<210> SEQ ID NO 1
<211> LENGTH: 840
<212> TYPE: PRT
<213> ORGANISM: Canavalia ensiformis

<400> SEQUENCE: 1

Met Lys Leu Ser Pro Arg Glu Val Glu Lys Leu Gly Leu His Asn Ala
1               5                   10                  15

Gly Tyr Leu Ala Gln Lys Arg Leu Ala Arg Gly Val Arg Leu Asn Tyr
            20                  25                  30

Thr Glu Ala Val Ala Leu Ile Ala Ser Gln Ile Met Glu Tyr Ala Arg
        35                  40                  45

Asp Gly Glu Lys Thr Val Ala Gln Leu Met Cys Leu Gly Gln His Leu
    50                  55                  60

Leu Gly Arg Arg Gln Val Leu Pro Ala Val Pro His Leu Leu Asn Ala
65                  70                  75                  80

Val Gln Val Glu Ala Thr Phe Pro Asp Gly Thr Lys Leu Val Thr Val
                85                  90                  95

His Asp Pro Ile Ser Arg Glu Asn Gly Glu Leu Gln Glu Ala Leu Phe
            100                 105                 110

Gly Ser Leu Leu Pro Val Pro Ser Leu Asp Lys Phe Ala Glu Thr Lys
        115                 120                 125

Glu Asp Asn Arg Ile Pro Gly Glu Ile Leu Cys Glu Asp Glu Cys Leu
    130                 135                 140

Thr Leu Asn Ile Gly Arg Lys Ala Val Ile Leu Lys Val Thr Ser Lys
145                 150                 155                 160

Gly Asp Arg Pro Ile Gln Val Gly Ser His Tyr His Phe Ile Glu Val
                165                 170                 175

Asn Pro Tyr Leu Thr Phe Asp Arg Arg Lys Ala Tyr Gly Met Arg Leu
            180                 185                 190

Asn Ile Ala Ala Gly Thr Ala Val Arg Phe Glu Pro Gly Asp Cys Lys
        195                 200                 205

Ser Val Thr Leu Val Ser Ile Glu Gly Asn Lys Val Ile Arg Gly Gly
    210                 215                 220

Asn Ala Ile Ala Asp Gly Pro Val Asn Glu Thr Asn Leu Glu Ala Ala
225                 230                 235                 240

Met His Ala Val Arg Ser Lys Gly Phe Gly His Glu Glu Lys Asp
                245                 250                 255

Ala Ser Glu Gly Phe Thr Lys Glu Asp Pro Asn Cys Pro Phe Asn Thr
            260                 265                 270

-continued

Phe Ile His Arg Lys Glu Tyr Ala Asn Lys Tyr Gly Pro Thr Thr Gly
            275                 280                 285

Asp Lys Ile Arg Leu Gly Asp Thr Asn Leu Leu Ala Glu Ile Glu Lys
290                 295                 300

Asp Tyr Ala Leu Tyr Gly Asp Glu Cys Val Phe Gly Gly Lys Val
305                 310                 315                 320

Ile Arg Asp Gly Met Gly Gln Ser Cys Gly His Pro Pro Ala Ile Ser
                325                 330                 335

Leu Asp Thr Val Ile Thr Asn Ala Val Ile Asp Tyr Thr Gly Ile
                340                 345                 350

Ile Lys Ala Asp Ile Gly Ile Lys Asp Gly Leu Ile Ala Ser Ile Gly
            355                 360                 365

Lys Ala Gly Asn Pro Asp Ile Met Asn Gly Val Phe Ser Asn Met Ile
370                 375                 380

Ile Gly Ala Asn Thr Glu Val Ile Ala Gly Glu Gly Leu Ile Val Thr
385                 390                 395                 400

Ala Gly Ala Ile Asp Cys His Val His Tyr Ile Cys Pro Gln Leu Val
                405                 410                 415

Tyr Glu Ala Ile Ser Ser Gly Ile Thr Thr Leu Val Gly Gly Gly Thr
                420                 425                 430

Gly Pro Ala Ala Gly Thr Arg Ala Thr Thr Cys Thr Pro Ser Pro Thr
            435                 440                 445

Gln Met Arg Leu Met Leu Gln Ser Thr Asp Asp Leu Pro Leu Asn Phe
            450                 455                 460

Gly Phe Thr Gly Lys Gly Ser Ser Ser Lys Pro Asp Glu Leu His Glu
465                 470                 475                 480

Ile Ile Lys Ala Gly Ala Met Gly Leu Lys Leu His Glu Asp Trp Gly
                485                 490                 495

Ser Thr Pro Ala Ala Ile Asp Asn Cys Leu Thr Ile Ala Glu His His
            500                 505                 510

Asp Ile Gln Ile Asn Ile His Thr Asp Thr Leu Asn Glu Ala Gly Phe
            515                 520                 525

Val Glu His Ser Ile Ala Ala Phe Lys Gly Arg Thr Ile His Thr Tyr
530                 535                 540

His Ser Glu Gly Ala Gly Gly His Ala Pro Asp Ile Ile Lys Val
545                 550                 555                 560

Cys Gly Ile Lys Asn Val Leu Pro Ser Ser Thr Asn Pro Thr Arg Pro
                565                 570                 575

Leu Thr Ser Asn Thr Ile Asp Glu His Leu Asp Met Leu Met Val Cys
            580                 585                 590

His His Leu Asp Arg Glu Ile Pro Glu Asp Leu Ala Phe Ala His Ser
            595                 600                 605

Arg Ile Arg Lys Lys Thr Ile Ala Ala Glu Asp Val Leu Asn Asp Ile
610                 615                 620

Gly Ala Ile Ser Ile Ile Ser Ser Asp Ser Gln Ala Met Gly Arg Val
625                 630                 635                 640

Gly Glu Val Ile Ser Arg Thr Trp Gln Thr Ala Asp Lys Met Lys Ala
                645                 650                 655

Gln Thr Gly Pro Leu Lys Cys Asp Ser Ser Asp Asn Asp Asn Phe Arg
            660                 665                 670

Ile Arg Arg Tyr Ile Ala Lys Tyr Thr Ile Asn Pro Ala Ile Ala Asn
            675                 680                 685

Gly Phe Ser Gln Tyr Val Gly Ser Val Glu Val Gly Lys Leu Ala Asp

```
                690             695             700
Leu Val Met Trp Lys Pro Ser Phe Phe Gly Thr Lys Pro Glu Met Val
705                 710                 715                 720

Ile Lys Gly Gly Met Val Ala Trp Ala Asp Ile Gly Asp Pro Asn Ala
                725                 730                 735

Ser Ile Pro Thr Pro Glu Pro Val Lys Met Arg Pro Met Tyr Gly Thr
            740                 745                 750

Leu Gly Lys Ala Gly Gly Ala Leu Ser Ile Ala Phe Val Ser Lys Ala
            755                 760                 765

Ala Leu Asp Gln Arg Val Asn Val Leu Tyr Gly Leu Asn Lys Arg Val
        770                 775                 780

Glu Ala Val Ser Asn Val Arg Lys Leu Thr Lys Leu Asp Met Lys Leu
785                 790                 795                 800

Asn Asp Ala Leu Pro Glu Ile Thr Val Asp Pro Glu Ser Tyr Thr Val
                805                 810                 815

Lys Ala Asp Gly Lys Leu Leu Cys Val Ser Glu Ala Thr Thr Val Pro
            820                 825                 830

Leu Ser Arg Asn Tyr Phe Leu Phe
            835                 840

<210> SEQ ID NO 2
<211> LENGTH: 837
<212> TYPE: PRT
<213> ORGANISM: Glycine max

<400> SEQUENCE: 2

Met Lys Leu Ser Pro Arg Glu Ile Glu Lys Leu Asp Leu His Asn Ala
1               5                   10                  15

Gly Tyr Leu Ala Gln Lys Arg Leu Ala Arg Gly Leu Arg Leu Asn Tyr
            20                  25                  30

Val Glu Thr Val Ala Leu Ile Ala Thr Gln Ile Leu Glu Phe Val Arg
        35                  40                  45

Asp Gly Glu Lys Thr Val Ala Gln Leu Met Cys Ile Gly Arg Glu Leu
    50                  55                  60

Leu Gly Arg Lys Gln Val Leu Pro Ala Val Pro His Leu Val Glu Ser
65                  70                  75                  80

Val Gln Val Glu Ala Thr Phe Arg Asp Gly Thr Lys Leu Val Thr Ile
                85                  90                  95

His Asp Leu Phe Ala Cys Glu Asn Gly Asn Leu Glu Leu Ala Leu Phe
            100                 105                 110

Gly Ser Phe Leu Pro Val Pro Ser Leu Asp Lys Phe Thr Glu Asn Glu
        115                 120                 125

Glu Asp His Arg Thr Pro Gly Glu Ile Ile Cys Arg Ser Glu Asn Leu
    130                 135                 140

Ile Leu Asn Pro Arg Arg Asn Ala Ile Ile Leu Arg Val Val Asn Lys
145                 150                 155                 160

Gly Asp Arg Pro Ile Gln Val Gly Ser His Tyr His Phe Ile Glu Val
                165                 170                 175

Asn Pro Tyr Leu Thr Phe Asp Arg Arg Lys Ala Tyr Gly Met Arg Leu
            180                 185                 190

Asn Ile Ala Ala Gly Asn Ala Thr Arg Phe Glu Pro Gly Glu Cys Lys
        195                 200                 205

Ser Val Val Leu Val Ser Ile Gly Gly Asn Lys Val Ile Arg Gly Gly
    210                 215                 220
```

-continued

Asn Asn Ile Ala Asp Gly Pro Val Asn Asp Ser Asn Cys Arg Ala Ala
225                 230                 235                 240

Met Lys Ala Val Val Thr Arg Gly Phe Gly His Val Glu Glu Glu Asn
            245                 250                 255

Ala Arg Glu Gly Val Thr Gly Glu Asp Tyr Ser Leu Thr Thr Val Ile
        260                 265                 270

Ser Arg Glu Glu Tyr Ala His Lys Tyr Gly Pro Thr Thr Gly Asp Lys
    275                 280                 285

Ile Arg Leu Gly Asp Thr Asp Leu Phe Ala Glu Ile Glu Lys Asp Phe
290                 295                 300

Ala Val Tyr Gly Asp Glu Cys Val Phe Gly Gly Lys Val Ile Arg
305                 310                 315                 320

Asp Gly Met Gly Gln Ser Ser Gly His Pro Pro Glu Gly Ser Leu Asp
            325                 330                 335

Thr Val Ile Thr Asn Ala Val Ile Ile Asp Tyr Thr Gly Ile Ile Lys
        340                 345                 350

Ala Asp Ile Gly Ile Lys Asp Gly Leu Ile Ile Ser Thr Gly Lys Ala
    355                 360                 365

Gly Asn Pro Asp Ile Met Asn Asp Val Phe Pro Asn Met Ile Ile Gly
370                 375                 380

Ala Asn Thr Glu Val Ile Ala Gly Glu Gly Leu Ile Val Thr Ala Gly
385                 390                 395                 400

Ala Ile Asp Cys His Val His Phe Ile Cys Pro Gln Leu Val Tyr Asp
            405                 410                 415

Ala Val Thr Ser Gly Ile Thr Thr Leu Val Gly Gly Thr Gly Pro
        420                 425                 430

Ala Asp Gly Thr Arg Ala Thr Thr Cys Thr Pro Ala Pro Asn Gln Met
    435                 440                 445

Lys Leu Met Leu Gln Ser Thr Asp Asp Met Pro Leu Asn Phe Gly Phe
450                 455                 460

Thr Gly Lys Gly Asn Ser Ala Lys Pro Asp Glu Leu His Glu Ile Ile
465                 470                 475                 480

Arg Ala Gly Ala Met Gly Leu Lys Leu His Glu Asp Trp Gly Thr Thr
            485                 490                 495

Pro Ala Ala Ile Asp Ser Cys Leu Thr Val Ala Asp Gln Tyr Asp Ile
        500                 505                 510

Gln Val Asn Ile His Thr Asp Thr Leu Asn Glu Ser Gly Phe Val Glu
    515                 520                 525

His Thr Ile Ala Ala Phe Lys Gly Arg Thr Ile His Thr Tyr His Ser
530                 535                 540

Glu Gly Ala Gly Gly Gly His Ala Pro Asp Ile Ile Lys Val Cys Gly
545                 550                 555                 560

Glu Lys Asn Val Leu Pro Ser Ser Thr Asn Pro Thr Arg Pro Tyr Thr
            565                 570                 575

His Asn Thr Ile Asp Glu His Leu Asp Met Leu Met Val Cys His His
        580                 585                 590

Leu Asn Lys Asn Ile Pro Glu Asp Val Ala Phe Ala Glu Ser Arg Ile
    595                 600                 605

Arg Ala Glu Thr Ile Ala Ala Glu Asp Ile Leu His Asp Lys Gly Ala
610                 615                 620

Ile Ser Ile Ile Ser Ser Asp Ser Gln Ala Met Gly Arg Ile Gly Glu
625                 630                 635                 640

Val Ile Ser Arg Thr Trp Gln Thr Ala Asp Lys Met Lys Ser Gln Arg

-continued

```
                645                 650                 655
Gly Pro Leu Gln Pro Gly Glu Asp Asn Asp Asn Phe Arg Ile Lys Arg
            660                 665                 670
Tyr Val Ala Lys Tyr Thr Ile Asn Pro Ala Ile Ala Asn Gly Leu Ser
        675                 680                 685
Gln Tyr Val Gly Ser Val Glu Ala Gly Lys Leu Ala Asp Leu Val Leu
    690                 695                 700
Trp Lys Pro Ser Phe Phe Gly Ala Lys Pro Glu Met Val Ile Lys Gly
705                 710                 715                 720
Gly Glu Val Ala Tyr Ala Asn Met Gly Asp Pro Asn Ala Ser Ile Pro
                725                 730                 735
Thr Pro Glu Pro Val Ile Met Arg Pro Met Phe Gly Ala Phe Gly Lys
            740                 745                 750
Ala Gly Ser Ser His Ser Ile Ala Phe Val Ser Lys Ala Ala Leu Asp
        755                 760                 765
Glu Gly Val Lys Ala Ser Tyr Gly Leu Asn Lys Arg Val Glu Ala Val
    770                 775                 780
Lys Asn Val Arg Lys Leu Thr Lys Arg Asp Met Lys Leu Asn Asp Thr
785                 790                 795                 800
Leu Pro Gln Ile Thr Val Asp Pro Glu Thr Tyr Thr Val Thr Ala Asp
                805                 810                 815
Gly Glu Val Leu Thr Cys Thr Ala Ala Lys Thr Val Pro Leu Ser Arg
            820                 825                 830
Asn Tyr Phe Leu Phe
        835

<210> SEQ ID NO 3
<211> LENGTH: 838
<212> TYPE: PRT
<213> ORGANISM: Agaricus bisporus

<400> SEQUENCE: 3

Met Arg Leu Leu Pro Arg Glu Glu Ala Lys Val Leu His Gln Val
1               5                   10                  15
Gly Phe Ile Ala Gln Lys Arg Leu Ala Arg Gly Val Lys Leu Asn Lys
            20                  25                  30
Thr Glu Ala Val Ala Leu Ile Ala Ser Val Leu Gln Glu Arg Ile Arg
        35                  40                  45
Asp Gly Arg His Ser Val Ala Glu Leu Met Gln His Gly Lys Lys Ile
    50                  55                  60
Leu Gly Arg Arg His Val Leu Pro Asp Val Pro Ala Leu Leu His Glu
65                  70                  75                  80
Ile Gln Val Glu Gly Thr Phe Leu Asp Gly Val Phe Leu Val Thr Val
                85                  90                  95
His Gln Pro Ile Cys Thr Glu Asp Gly Asp Leu Glu Ala Ala Leu Tyr
            100                 105                 110
Gly Ser Phe Leu Pro Ile Pro Pro Gln Asp Asp Phe Pro Val Ala Pro
        115                 120                 125
Asp Ser Asp Tyr Leu Pro Glu Lys Thr Ala Gly Ala Ile Ile Pro Lys
    130                 135                 140
Gln Glu Asp Ile Val Leu Asn Gln Gly Arg Glu Arg Ile Arg Leu Arg
145                 150                 155                 160
Ile Thr Asn Thr Gly Asp Arg Pro Ile Gln Val Gly Ser His Tyr His
                165                 170                 175
```

```
Phe Ile Glu Thr Asn Arg Ala Leu Ser Phe Asp Arg Leu Lys Ser Tyr
            180                 185                 190
Gly Lys Arg Leu Asp Ile Ala Ala Gly Thr Ala Val Arg Phe Glu Pro
        195                 200                 205
Gly Asp Thr Lys Ala Val Thr Leu Val Ser Ile Ser Gly Asn Lys Val
    210                 215                 220
Ile Ser Gly Gly Asn Ser Leu Ala Ser Gly His Ile Gly Thr Phe Arg
225                 230                 235                 240
Ser Glu Val Leu Leu Glu Asp Ile Leu Arg Arg Asp Phe Ala His Val
                245                 250                 255
Ser Glu Pro Gly Ala Leu Glu Val Met Glu Asp Thr Lys Ile Gly Arg
            260                 265                 270
Glu Thr Tyr Ile Ser Met Tyr Gly Pro Thr Val Gly Asp Arg Val Arg
        275                 280                 285
Leu Gly Asp Thr Glu Leu Trp Ile Glu Val Glu His Asp Glu Thr Val
    290                 295                 300
Tyr Gly Asp Glu Val Lys Phe Gly Gly Gly Lys Val Ile Arg Glu Gly
305                 310                 315                 320
Met Gly Gln Ala Thr Asn Arg Ser Ser Asn Glu Thr Leu Asp Leu Val
                325                 330                 335
Ile Thr Asn Ala Leu Ile Val Asp Trp Ser Gly Ile Tyr Lys Ala Asp
            340                 345                 350
Ile Gly Val Lys Asn Gly Phe Ile Cys Gly Ile Gly Lys Ala Gly Asn
        355                 360                 365
Pro Asp Val Met Ser Asn Ile His Pro Thr Leu Val Ile Gly Ser Ser
    370                 375                 380
Thr Glu Val Ile Ala Gly Glu Lys Leu Ile Ile Thr Ala Gly Gly Ile
385                 390                 395                 400
Asp Thr His Ile His Phe Ile Cys Pro Gln Leu Val Asp Glu Ala Leu
                405                 410                 415
Ala Ser Gly Leu Thr Thr Leu Ile Gly Gly Gly Thr Gly Pro Ser Ala
            420                 425                 430
Gly Thr Asn Ala Thr Thr Cys Thr Pro Ser Pro Phe Tyr Met Arg His
        435                 440                 445
Met Leu Ala Ala Thr Asp Gly Leu Pro Met Asn Phe Gly Phe Thr Gly
    450                 455                 460
Lys Gly Asn Asp Ala Gly Pro Thr Ala Ile Glu Glu Ile Val Arg Ala
465                 470                 475                 480
Gly Ala Ser Gly Leu Lys Leu His Glu Asp Trp Gly Thr Thr Pro Ala
                485                 490                 495
Ala Ile Arg Asn Cys Leu Asp Val Ala Asp Lys Tyr Asp Val Gln Val
            500                 505                 510
Thr Ile His Thr Asp Thr Leu Asn Glu Ser Gly Phe Val Glu Ser Thr
        515                 520                 525
Ile Glu Ala Phe Gly Gly Arg Thr Ile His Thr Tyr His Thr Glu Gly
    530                 535                 540
Ala Gly Gly Gly His Ala Pro Asp Ile Ile Val Val Cys Gly Gln Asn
545                 550                 555                 560
Asn Val Leu Pro Ser Ser Thr Asn Pro Thr Arg Pro Tyr Ala Lys Asn
                565                 570                 575
Thr Leu Asp Glu His Leu Asp Met Leu Met Val Cys His His Leu Asp
            580                 585                 590
Lys Ser Ile Pro Glu Asp Leu Asp Phe Ala Glu Ser Arg Ile Arg Ala
```

```
                595                 600                 605
Glu Thr Val Ala Ala Glu Asp Val Leu His Asp Ile Gly Ala Ile Ser
610                 615                 620
Met Ile Ser Ser Asp Ser Gln Ala Met Gly Arg Ile Gly Glu Val Ile
625                 630                 635                 640
Ser Arg Thr Trp Arg Thr Ala Ser Lys Met Arg Glu Val Arg Gly Pro
            645                 650                 655
Leu Thr Asp Leu Gly Asp Asp Gly Arg Lys Asp Asn Ala Arg Val Lys
            660                 665                 670
Arg Tyr Ile Ala Lys Tyr Thr Val Asn Pro Ala Ile Ala His Gly Ile
            675                 680                 685
Ser His Leu Val Gly His Val Ala Val Gly Thr Leu Ala Asp Leu Val
            690                 695                 700
Leu Trp Lys Pro Glu Asn Phe Gly Ser Lys Pro Glu Met Ile Leu Lys
705                 710                 715                 720
Ala Gly Val Ile Thr Tyr Ser Gln Met Gly Asp Ala Asn Ala Ser Ile
                725                 730                 735
Pro Ser Val Gln Pro Phe Tyr Ser Lys Pro Met Trp Gly Ala Lys Pro
            740                 745                 750
Gly Ser Ala Ala Leu Asn Ser Val Ala Phe Val Ser Gln Val Ser Ile
            755                 760                 765
Thr Ser Arg Val Ile Glu Ser Tyr Gly Leu Ser Lys Lys Ile Glu Ala
            770                 775                 780
Val Arg Gly Cys Arg Asp Ile Gly Lys Lys Asp Met Lys Trp Asn Asp
785                 790                 795                 800
Thr Thr Pro Ala Met Lys Val Asp Pro Glu Ser Tyr Glu Val Arg Ala
                805                 810                 815
Asp Gly Val Leu Met Asp Val Lys Pro Val Glu Arg Val Ala Leu Ala
            820                 825                 830
Thr Pro Tyr Asn Leu Phe
            835

<210> SEQ ID NO 4
<211> LENGTH: 835
<212> TYPE: PRT
<213> ORGANISM: Schizosaccharomyces pombe

<400> SEQUENCE: 4

Met Gln Pro Arg Glu Leu His Lys Leu Thr Leu His Gln Leu Gly Ser
1               5                   10                  15
Leu Ala Gln Lys Arg Leu Cys Arg Gly Val Lys Leu Asn Lys Leu Glu
                20                  25                  30
Ala Thr Ser Leu Ile Ala Ser Gln Ile Gln Glu Tyr Val Arg Asp Gly
            35                  40                  45
Asn His Ser Val Ala Asp Leu Met Ser Leu Gly Lys Asp Met Leu Gly
        50                  55                  60
Lys Arg His Val Gln Pro Asn Val Val His Leu His Glu Ile Met
65                  70                  75                  80
Ile Glu Ala Thr Phe Pro Asp Gly Thr Tyr Leu Ile Thr Ile His Asp
                85                  90                  95
Pro Ile Cys Thr Thr Asp Gly Asn Leu Glu His Ala Leu Tyr Gly Ser
                100                 105                 110
Phe Leu Pro Thr Pro Ser Gln Glu Leu Phe Pro Leu Glu Glu Glu Lys
            115                 120                 125
```

```
Leu Tyr Ala Pro Glu Asn Ser Pro Gly Phe Val Glu Val Leu Glu Gly
    130                 135                 140
Glu Ile Glu Leu Leu Pro Asn Leu Pro Arg Thr Pro Ile Glu Val Arg
145                 150                 155                 160
Asn Met Gly Asp Arg Pro Ile Gln Val Gly Ser His Tyr His Phe Ile
                165                 170                 175
Glu Thr Asn Glu Lys Leu Cys Phe Asp Arg Ser Lys Ala Tyr Gly Lys
            180                 185                 190
Arg Leu Asp Ile Pro Ser Gly Thr Ala Ile Arg Phe Glu Pro Gly Val
        195                 200                 205
Met Lys Ile Val Asn Leu Ile Pro Ile Gly Ala Lys Leu Ile Gln
210                 215                 220
Gly Gly Asn Ser Leu Ser Lys Gly Val Phe Asp Asp Ser Arg Thr Arg
225                 230                 235                 240
Glu Ile Val Asp Asn Leu Met Lys Gln Gly Phe Met His Gln Pro Glu
                245                 250                 255
Ser Pro Leu Asn Met Pro Leu Gln Ser Ala Arg Pro Phe Val Val Pro
            260                 265                 270
Arg Lys Leu Tyr Ala Val Met Tyr Gly Pro Thr Thr Asn Asp Lys Ile
        275                 280                 285
Arg Leu Gly Asp Thr Asn Leu Ile Val Arg Val Glu Lys Asp Phe Thr
    290                 295                 300
Glu Tyr Gly Asn Glu Ser Val Phe Gly Gly Lys Val Ile Arg Asp
305                 310                 315                 320
Gly Thr Gly Gln Ser Ser Lys Ser Met Asp Glu Cys Leu Asp Thr
                325                 330                 335
Val Ile Thr Asn Ala Val Ile Ile Asp His Thr Gly Ile Tyr Lys Ala
            340                 345                 350
Asp Ile Gly Ile Lys Asn Gly Tyr Ile Val Gly Ile Gly Lys Ala Gly
        355                 360                 365
Asn Pro Asp Thr Met Asp Asn Ile Gly Glu Asn Met Val Ile Gly Ser
    370                 375                 380
Ser Thr Asp Val Ile Ser Ala Glu Asn Lys Ile Val Thr Tyr Gly Gly
385                 390                 395                 400
Met Asp Ser His Val His Phe Ile Cys Pro Gln Gln Ile Glu Glu Ala
                405                 410                 415
Leu Ala Ser Gly Ile Thr Thr Met Tyr Gly Gly Thr Gly Pro Ser
            420                 425                 430
Thr Gly Thr Asn Ala Thr Thr Cys Thr Pro Asn Lys Asp Leu Ile Arg
        435                 440                 445
Ser Met Leu Arg Ser Thr Asp Ser Tyr Pro Met Asn Ile Gly Leu Thr
    450                 455                 460
Gly Lys Gly Asn Asp Ser Gly Ser Ser Ser Leu Lys Glu Gln Ile Glu
465                 470                 475                 480
Ala Gly Cys Ser Gly Leu Lys Leu His Glu Asp Trp Gly Ser Thr Pro
                485                 490                 495
Ala Ala Ile Asp Ser Cys Leu Ser Val Cys Asp Glu Tyr Asp Val Gln
            500                 505                 510
Cys Leu Ile His Thr Asp Thr Leu Asn Glu Ser Ser Phe Val Glu Gly
        515                 520                 525
Thr Phe Lys Ala Phe Lys Asn Arg Thr Ile His Thr Tyr His Val Glu
    530                 535                 540
Gly Ala Gly Gly Gly His Ala Pro Asp Ile Ile Ser Leu Val Gln Asn
```

```
545                 550                 555                 560

Pro Asn Ile Leu Pro Ser Ser Thr Asn Pro Thr Arg Pro Phe Thr Thr
                565                 570                 575

Asn Thr Leu Asp Glu Glu Leu Asp Met Leu Met Val Cys His His Leu
                580                 585                 590

Ser Arg Asn Val Pro Glu Asp Val Ala Phe Ala Glu Ser Arg Ile Arg
                595                 600                 605

Ala Glu Thr Ile Ala Ala Glu Asp Ile Leu Gln Asp Leu Gly Ala Ile
                610                 615                 620

Ser Met Ile Ser Ser Asp Ser Gln Ala Met Gly Arg Cys Gly Glu Val
625                 630                 635                 640

Ile Ser Arg Thr Trp Lys Thr Ala His Lys Asn Lys Leu Gln Arg Gly
                645                 650                 655

Ala Leu Pro Glu Asp Glu Gly Ser Gly Val Asp Asn Phe Arg Val Lys
                660                 665                 670

Arg Tyr Val Ser Lys Tyr Thr Ile Asn Pro Ala Ile Thr His Gly Ile
                675                 680                 685

Ser His Ile Val Gly Ser Val Glu Ile Gly Lys Phe Ala Asp Leu Val
                690                 695                 700

Leu Trp Asp Phe Ala Asp Phe Gly Ala Arg Pro Ser Met Val Leu Lys
705                 710                 715                 720

Gly Gly Met Ile Ala Leu Ala Ser Met Gly Asp Pro Asn Gly Ser Ile
                725                 730                 735

Pro Thr Val Ser Pro Leu Met Ser Trp Gln Met Phe Gly Ala His Asp
                740                 745                 750

Pro Glu Arg Ser Ile Ala Phe Val Ser Lys Ala Ser Ile Thr Ser Gly
                755                 760                 765

Val Ile Glu Ser Tyr Gly Leu His Lys Arg Val Glu Ala Val Lys Ser
                770                 775                 780

Thr Arg Asn Ile Gly Lys Lys Asp Met Val Tyr Asn Ser Tyr Met Pro
785                 790                 795                 800

Lys Met Thr Val Asp Pro Glu Ala Tyr Thr Val Thr Ala Asp Gly Lys
                805                 810                 815

Val Met Glu Cys Glu Pro Val Asp Lys Leu Pro Leu Ser Gln Ser Tyr
                820                 825                 830

Phe Ile Phe
        835

<210> SEQ ID NO 5
<211> LENGTH: 569
<212> TYPE: PRT
<213> ORGANISM: Bacillus pasteurii

<400> SEQUENCE: 5

Met Lys Ile Asn Arg Gln Gln Tyr Ala Glu Ser Tyr Gly Pro Thr Val
1               5                   10                  15

Gly Asp Arg Val Arg Leu Ala Asp Thr Asp Leu Gly Glu Val Glu Lys
                20                  25                  30

Asp Tyr Tyr Tyr Leu Gly Asp Glu Val Asn Phe Gly Gly Gly Lys Val
            35                  40                  45

Leu Arg Glu Gly Met Gly Glu Asn Gly Thr Tyr Thr Arg Thr Glu Asn
        50                  55                  60

Val Leu Asp Leu Leu Thr Asn Ala Leu Ile Leu Asp Tyr Thr Gly
65                  70                  75                  80
```

-continued

```
Ile Tyr Lys Ala Asp Ile Gly Val Lys Asp Gly Tyr Ile Val Gly Ile
                 85                  90                  95
Gly Lys Gly Gly Asn Pro Asp Ile Met Asp Gly Val Thr Pro Asn Met
            100                 105                 110
Ile Val Gly Thr Ala Thr Glu Val Ile Ala Ala Glu Gly Lys Ile Val
            115                 120                 125
Thr Ala Gly Gly Ile Asp Thr His Val His Phe Ile Asn Pro Asp Gln
        130                 135                 140
Val Asp Val Ala Leu Ala Asn Gly Ile Thr Thr Leu Phe Gly Gly Gly
145                 150                 155                 160
Thr Gly Pro Ala Glu Gly Ser Lys Ala Thr Thr Val Thr Pro Gly Pro
                165                 170                 175
Trp Asn Ile Glu Lys Met Leu Lys Ser Thr Glu Gly Leu Pro Ile Asn
            180                 185                 190
Val Gly Ile Leu Gly Lys Gly His Gly Ser Ser Ile Ala Pro Ile Met
            195                 200                 205
Glu Gln Ile Asp Ala Gly Ala Ala Gly Leu Lys Ile His Glu Asp Trp
        210                 215                 220
Gly Ala Thr Pro Ala Ser Ile Asp Arg Ser Leu Thr Val Ala Asp Glu
225                 230                 235                 240
Ala Asp Val Gln Val Ala Ile His Ser Asp Thr Leu Asn Glu Ala Gly
                245                 250                 255
Phe Leu Glu Asp Thr Val Arg Ala Ile Asn Gly Arg Val Ile His Ser
            260                 265                 270
Phe His Val Glu Gly Ala Gly Gly Gly His Ala Pro Asp Ile Met Ala
            275                 280                 285
Met Ala Gly His Pro Asn Val Leu Pro Ser Ser Thr Asn Pro Thr Arg
        290                 295                 300
Pro Phe Thr Val Asn Thr Ile Asp Glu His Leu Asp Met Leu Met Val
305                 310                 315                 320
Cys His His Leu Lys Gln Asn Ile Pro Glu Asp Val Ala Phe Ala Asp
                325                 330                 335
Ser Arg Ile Arg Pro Glu Thr Ile Ala Ala Glu Asp Ile Leu His Asp
            340                 345                 350
Leu Gly Ile Ile Ser Met Met Ser Thr Asp Ala Leu Ala Met Gly Arg
            355                 360                 365
Ala Gly Glu Met Val Leu Arg Thr Trp Gln Thr Ala Asp Lys Met Lys
        370                 375                 380
Lys Gln Arg Gly Pro Leu Ala Glu Glu Lys Asn Gly Ser Asp Asn Phe
385                 390                 395                 400
Arg Leu Lys Arg Tyr Val Ser Lys Tyr Thr Ile Asn Pro Ala Ile Ala
                405                 410                 415
Gln Gly Met Ala His Glu Val Gly Ser Ile Glu Glu Gly Lys Phe Ala
            420                 425                 430
Asp Leu Val Leu Trp Glu Pro Lys Phe Phe Gly Val Lys Ala Asp Arg
            435                 440                 445
Val Ile Lys Gly Gly Ile Ile Ala Tyr Ala Gln Ile Gly Asp Pro Ser
        450                 455                 460
Ala Ser Ile Pro Thr Pro Gln Pro Val Met Gly Arg Arg Met Tyr Gly
465                 470                 475                 480
Thr Val Gly Asp Leu Ile His Asp Thr Asn Ile Thr Phe Met Ser Lys
                485                 490                 495
Ser Ser Ile Gln Gln Gly Val Pro Ala Lys Leu Gly Leu Lys Arg Arg
```

```
            500                 505                 510
Ile Gly Thr Val Lys Asn Cys Arg Asn Ile Gly Lys Lys Asp Met Lys
            515                 520                 525

Trp Asn Asp Val Thr Thr Asp Ile Asp Ile Asn Pro Glu Thr Tyr Glu
        530                 535                 540

Val Lys Val Asp Gly Glu Val Leu Thr Cys Glu Pro Val Lys Glu Leu
545                 550                 555                 560

Pro Met Ala Gln Arg Tyr Phe Leu Phe
                565

<210> SEQ ID NO 6
<211> LENGTH: 566
<212> TYPE: PRT
<213> ORGANISM: Pseudomonas syringae

<400> SEQUENCE: 6

Met Lys Ile Ser Arg Gln Ala Tyr Ala Asp Met Phe Gly Pro Thr Val
1               5                   10                  15

Gly Asp Lys Val Arg Leu Ala Asp Thr Glu Leu Trp Ile Glu Val Glu
            20                  25                  30

Lys Asp Phe Thr Thr Tyr Gly Glu Glu Val Lys Phe Gly Gly Gly Lys
        35                  40                  45

Val Ile Arg Asp Gly Met Gly Gln Gly Gln Leu Leu Ala Ala Glu Val
50                  55                  60

Val Asp Thr Leu Ile Thr Asn Ala Leu Ile Ile Asp His Trp Gly Ile
65                  70                  75                  80

Val Lys Ala Asp Val Gly Ile Lys Asn Gly Arg Ile Ala Ala Ile Gly
                85                  90                  95

Lys Ala Gly Asn Pro Asp Ile Gln Pro Asp Val Thr Ile Ala Val Gly
            100                 105                 110

Ala Ala Thr Glu Val Ile Ala Gly Glu Gly Met Ile Leu Thr Ala Gly
        115                 120                 125

Gly Val Asp Thr His Ile His Phe Ile Cys Pro Gln Gln Ile Glu Glu
    130                 135                 140

Ala Leu Met Ser Gly Val Thr Thr Met Ile Gly Gly Gly Thr Gly Pro
145                 150                 155                 160

Ala Thr Gly Thr Asn Ala Thr Thr Val Thr Pro Gly Pro Trp His Met
                165                 170                 175

Ala Arg Met Leu Gln Ala Ser Asp Ser Phe Pro Met Asn Ile Gly Phe
            180                 185                 190

Thr Gly Lys Gly Asn Val Ser Leu Pro Gly Pro Leu Ile Glu Gln Val
        195                 200                 205

Lys Ala Gly Ala Ile Gly Leu Lys Leu His Glu Asp Trp Gly Thr Thr
    210                 215                 220

Pro Ala Ala Ile Asp Asn Cys Leu Ser Val Ala Asp Glu Tyr Asp Val
225                 230                 235                 240

Gln Val Ala Ile His Thr Asp Thr Leu Asn Glu Ser Gly Phe Val Glu
                245                 250                 255

Thr Thr Leu Ala Ala Phe Lys Asn Arg Thr Ile His Thr Tyr His Thr
            260                 265                 270

Glu Gly Ala Gly Gly Gly His Ala Pro Asp Ile Ile Lys Ala Cys Gly
        275                 280                 285

Ser Pro Asn Val Leu Pro Ser Ser Thr Asn Pro Thr Arg Pro Phe Thr
    290                 295                 300
```

-continued

```
Arg Asn Thr Ile Asp Glu His Leu Asp Met Leu Met Val Cys His His
305                 310             315                 320

Leu Asp Pro Ser Ile Ala Glu Asp Val Ala Phe Ala Glu Ser Arg Ile
                325             330                 335

Arg Arg Glu Thr Ile Ala Ala Glu Asp Ile Leu His Asp Leu Gly Ala
            340             345                 350

Phe Ser Met Leu Ser Ser Asp Ser Gln Ala Met Gly Arg Val Gly Glu
        355             360                 365

Val Ile Met Arg Thr Trp Gln Thr Ala Asp Lys Met Lys Lys Gln Arg
370                 375             380

Gly Pro Leu Pro Gln Asp Gly Pro Gly Asn Asp Asn Phe Arg Ala Lys
385             390             395                 400

Arg Tyr Ile Ala Lys Tyr Thr Ile Asn Pro Ala Ile Thr His Gly Ile
            405             410                 415

Ser His Glu Val Gly Ser Ile Glu Val Gly Lys Trp Ala Asp Leu Val
            420             425                 430

Leu Trp Arg Pro Ala Phe Phe Gly Val Lys Pro Thr Leu Ile Leu Lys
        435             440             445

Gly Gly Ala Ile Ala Ala Ser Leu Met Gly Asp Ala Asn Ala Ser Ile
450             455             460

Pro Thr Pro Gln Pro Val His Tyr Arg Pro Met Phe Ala Ser Phe Gly
465             470             475                 480

Ser Ser Leu His Ala Thr Ser Leu Thr Phe Ile Ser Gln Ala Ala Phe
            485             490                 495

Asp Ala Gly Val Pro Glu Ser Leu Gly Leu Lys Lys Gln Ile Gly Val
            500             505             510

Val Lys Gly Cys Arg Thr Val Gln Lys Lys Asp Leu Ile His Asn Asp
        515             520             525

Tyr Leu Pro Asp Ile Glu Val Asp Pro Gln Thr Tyr Gln Val Lys Ala
        530             535             540

Asp Gly Val Leu Leu Trp Cys Glu Pro Ala Asp Val Leu Pro Met Ala
545             550             555                 560

Gln Arg Tyr Phe Leu Phe
                565
```

US 10,563,233 B2

CEMENTATION METHODS

CROSS REFERENCE

This application is a continuation in part of U.S. patent application Ser. No. 13/944,450, filed Jul. 17, 2013, which claims priority to U.S. Provisional Patent Application Ser. No. 61/672,597 filed Jul. 17, 2012, the disclosures of which are incorporated by reference herein in their entirety.

STATEMENT OF U.S. GOVERNMENT INTEREST

This invention was made with government support under 0856801 awarded by the National Science Foundation. The government has certain rights in the invention.

SUMMARY OF THE INVENTION

The present invention provides methods for mineral precipitation and/or cementation, comprising combining a column of a permeable starting material or a column of a non-porous but fractured starting material with a mixture comprising
  (a) isolated urease;
  (b) urea;
  (c) a source of divalent cations; and
  (d) an organic additive
wherein (a), (b), (c), and (d) are provided in amounts effective and the combining is carried out under conditions suitable to cause carbonate precipitation and/or cementation of the starting material within the column. In one embodiment, the methods are used for one or more of improving bearing capacity of foundations; reducing settlement potential of foundations or embankments; increasing lateral resistance of foundations; enhancing stability of slopes or embankments; reducing lateral earth pressures on retaining walls; increasing passive resistance of retaining walls; increasing capacity of ground anchors or soil nails; increasing the side resistance and tip resistance of deep foundations; facilitating tunneling in running or flowing ground; stabilizing excavations bottoms; soil erosion control; and groundwater control. In another embodiment, the starting material is selected from the group consisting of sand, silt, soil, clay, sediments, sawdust, fractured crystalline rocks, cracked concrete and sedimentary rocks including but not limited to conglomerate, breccia, sandstone, siltstone, shale, limestone, gypsum, and dolostone.

DETAILED DESCRIPTION OF THE INVENTION

Figure 1:
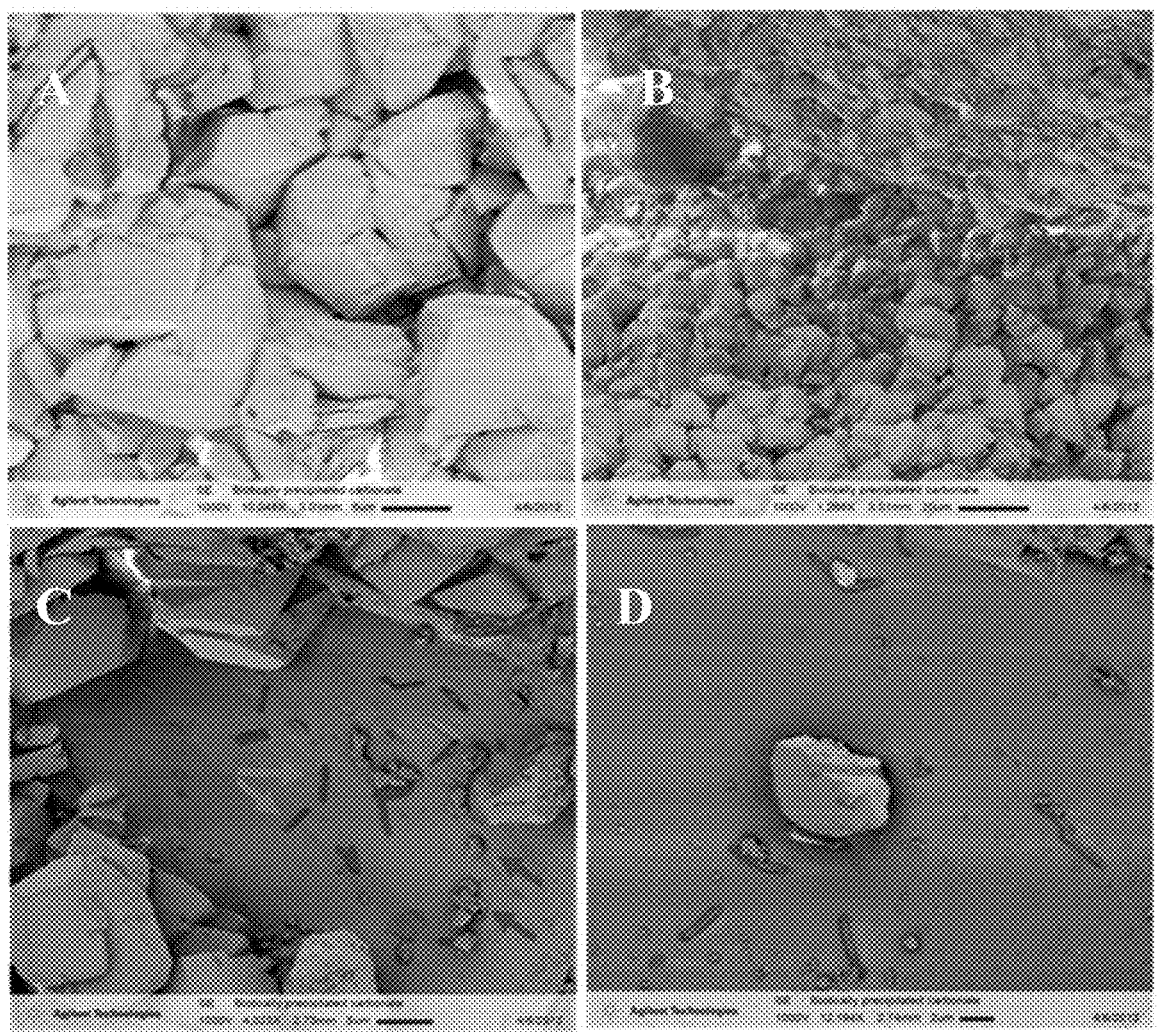
FIG. 1. Low-Voltage-Scanning electron microscope (LV-SEM) images of (a) Well-grown and cementing calcite crystals; (b) Cementing calcite crystals at inter-particle contact; (c) Indention of quartz surface (central arrows) and nucleation of calcite crystals (arrows on periphery); d.) Calcite crystal growing on quartz surface.

As used herein, the singular forms "a", "an" and "the" include plural referents unless the context clearly dictates otherwise. "And" as used herein is interchangeably used with "or" unless expressly stated otherwise.

All embodiments of any aspect of the invention can be used in combination, unless the context clearly dictates otherwise.

In a first aspect, the present invention provides mineral precipitation and/or host medium cementation methods, comprising combining a permeable starting material or a non-porous but fractured starting material with a mixture comprising
  (a) isolated urease;
  (b) urea;
  (c) a source of divalent cations; and
  (d) an organic additive
wherein (a), (b), (c), and (d) are provided in amounts effective and the combining is carried out under conditions suitable to cause carbonate precipitation and/or cementation of the starting material.

In a second aspect, the present invention provides mineral precipitation and/or cementation method for limiting erosion, comprising combining a permeable starting material or a non-porous but fractured starting material with
  (a) isolated urease;
  (b) urea;
  (c) a source of divalent cations;
  (d) an organic additive; and
  wherein (a), (b), (c) and (d) are provided in amounts effective and the combining is carried out under conditions suitable to cause carbonate precipitation and/or cementation of the starting material and wherein (a), (b), (c) and (d) are combined with the permeable starting material at the surface of the permeable starting material.

As used herein "limiting" refers to at a least 10% reduction in soil erosion compared to soil receiving no erosion treatment or control. Induced carbonate precipitation can enhance the stiffness, strength, and liquefaction resistance of soil. Methods currently under investigation for soil improvement by inducing carbonate precipitation are restricted to medium or coarser sands and are limited by the need to stimulate microbial growth either in the subsurface or ex situ in a reactor vessel and by plugging of the pores by carbonate precipitation and the microbial mass. The methods of the present invention provide significant advantages over prior methods, by permitting precipitation in and/or cementation of much finer permeable materials, such as fine sands and silts, than was previously possible. Furthermore, the methods of the invention mitigate plugging issues that plague prior methods. The methods provide an alternative to commonly used soil improvement techniques such as deep soil mixing, stone columns, penetration and compaction grouting, and rammed aggregate piers. The methods can also be used to fill in cracks in non-porous but fractured or fissured materials, including but not limited to rocks with fractures and cracked concrete.

The methods can be used, for example, in improving the bearing capacity of foundations, reducing settlement potential of foundations and embankments, increasing the lateral resistance of foundations, enhancing the stability of slopes and embankments, reducing lateral earth pressures on retaining walls, increasing the passive resistance of retaining walls, increasing the capacity of ground anchors and soil nails, increasing the side resistance and tip resistance of deep foundations, facilitating tunneling in running or flowing ground (dry or saturated cohesionless soil), stabilizing the bottom of excavations, soil erosion control, groundwater control, and sealing cracks in structural concrete or historical monuments.

"Carbonate cementation" means mineral precipitates that may include one or more cations such as calcium, magnesium, iron and others that may produce one of several phases of carbonate minerals, including but not limited to calcite. In a preferred embodiment, calcium carbonate precipitates form cementation bonds at inter-particle contacts in the permeable starting material. In particular embodiments, the calcium carbonate content of the column is less than 1.5%.

As used herein, "isolated urease" is urease that is purified away from cells and cellular materials. The urease may be synthetically produced or obtained and purified from any suitable source, including but not limited to bacteria, plants, invertebrates, and fungi. Urease enzyme as discussed herein is characterized by the reaction it catalyzes and identified by EC 3.5.1.5 (i.e. Reaction: urea+$H_2O$=$CO_2$+2 $NH_3$). In one embodiment, the urease enzyme is isolated from the jackbean plant (SEQ ID NO:1). The amino acid sequences of exemplary ureases for use with the present invention are provided below. However, it will be clear to those of skill in the art that any enzyme identified by EC 3.5.1.5 can be used in the methods of the invention, including but not limited to a urease comprising or consisting of any one of SEQ ID NOS: 2-5, where SEQ ID NO:2 is a soybean urease, SEQ ID NO:3 is a *Agaricus bisporus* urease, SEQ ID NO:4 is a *Schizosaccharomyces pombe* (strain 972/ATCC 24843) urease, SEQ ID NO:5 is a *Sporosarcina pasteurii* urease, and SEQ ID NO:6 is a *Pseudomonas syringae* (strain B728a) urease.

The appropriate amount of urease needed can be determined by one of skill in the art based on the teachings herein; factors to be considered in determining an appropriate amount of urease include, but are not limited to:

(a) urease source type (e.g. Jack bean vs. other source)

(b) urease purity, which dictates enzymatic activity (i.e. rate of conversion of urea to products); and (c) the stability/half-life of the enzyme matrix used, where the "enzyme matrix" refers to the specific form of the enzyme mixture used such as liquid, powder and/or solid when combined with or used apart from stabilizers, buffers, fillers or other media to facilitate its desired use.

For example, assuming that for practical purposes that transport via diffusion, advection and dispersion is not limiting the availability of urea or calcium to the enzymes—or vice versa—(e.g. we thoroughly mix the soil and cementation constituents or we actively pump the cementation constituents into the soil or do something to assure that the right constituents get to where they need to be), then in a homogenous soil (i.e. without zones of blocked flow or disproportionately high/preferential flow) we could expect an approximately linear relationship between urea conversion and required amount(s) of enzyme needed to convert "x" grams of urea by "y" grams of enzyme over a given time frame. If a soil mass requires a total amount "x" grams of urea to be converted into products for calcium carbonate formation, and "y" grams of enzyme can only convert 50% of "x" during its functional life time, then theoretically twice as much enzyme is needed to fully convert "x" grams of urea.

Urea is an organic compound of the chemical formula $CO(NH_2)_2$. Urea is a colorless, odorless, highly water soluble substance with very low toxicity (LD50=12 g/kg for mouse, Agrium MSDS), and is widely commercially available. Any suitable source of urea can be used, including but not limited to those disclosed herein.

The appropriate amount of urea can be determined by one of skill in the art based on the teachings herein; factors to be considered in determining an appropriate amount of urea include, but are not limited, to the amount of carbonate required as determined on a stoichiometric basis.

Several divalent cations, primarily alkaline earth metals (including but not limited to calcium and magnesium), that satisfy the crystalline structure constraints of calcite or calcium mineral carbonates can be used to precipitate carbonate minerals in the present methods. Any suitable source of divalent cations can be used, including but not limited to salts of organic and inorganic compounds such as nitrates, nitrites, chlorides, sulfates, oxides, acetates, silicates, oxalates or mixtures thereof.

The appropriate amount of ions can be determined by one of skill in the art based on the teachings herein; factors to be considered in determining an appropriate amount of ions include, but are not limited the required amount of carbonate precipitate as determined on a stoichiometric basis. In one non-limiting example, if 100 grams (approximately 1 mole) of calcium carbonate ($CaCO_3$) is desired, then 1 mole of urea (($NH_2)_2CO$) and 1 mole of calcium ($Ca^{2+}$) are required (the urea also provides the necessary 1 mole of carbon).

Any suitable permeable or non-porous starting material may be used in the methods of the invention, such as those having a particulate structure or those consisting of relatively impervious blocks delineated by an interconnected network of fractures or fissures. In a preferred embodiment, the starting material may be unconsolidated or partially consolidated particulate material such as sand, silt, soil, clay, sediments, sawdust or other material that is amenable to in situ cementation. In further embodiments, the starting material may be sedimentary rocks including but not limited to conglomerate, breccia, sandstone, siltstone, shale, limestone, gypsum, and dolostone. In one preferred embodiment, the starting material comprises sand. In another preferred embodiment, the starting material comprises silt. In a further preferred embodiment, the starting material is fractured crystalline rock or cracked concrete.

The starting material is "permeable" in that it enables sufficient passage of the isolated urease, the urea, and/or the source of calcium or other ions and constituents including, but not limited to, buffers and stabilizers, to enable carbonate precipitation with or without cementation.

The components can be combined in any way suitable in light of the specific starting material, the amount of starting material, the components to be used, etc. In various embodiments, the starting material and components are combined by a technique selected from the group consisting of flushing, injecting, spraying, pouring, dripping or trickling onto or into the starting material. The starting material may also be immersed in one or more ways as described above. In addition, secondary non-specific methods may be employed to facilitate carbonate precipitation including, but not limited to, moisture control measures, crystal seeding, and initiation of nucleation sites. In one embodiment, the methods comprise mixing powdered urease with the permeable starting material prior to percolation of a solution comprising the urea and the divalent ion source.

It will be understood by those of skill in the art that the step of "combining" the permeable starting material with effective amounts of isolated urease, urea, organic additive and ions covers any process that results in the bringing together of the four constituents in a manner that results in precipitation of carbonate minerals and/or cementation in the permeable starting material. The reactants may be added to the starting material simultaneously or sequentially. For example, there may be applications where one or two of the constituents are already present in the permeable starting material, in which case the step of "combining" will involve the addition of only the missing components. In one embodiment, the urea and ions are admixed and then added to the urease prior to application to the permeable starting material. However, it will be appreciated by those of skill in the art that the constituents may be combined in other ways to carry out the method of the invention.

By manipulating the relative effective amounts of the various components, the methods of the present invention enable the user to control carbonate precipitation and cementation by controlling the amount of carbonate formed and the rate at which it is formed. This flexibility means the methods of the present invention can be used in a wide range of applications from those that require a reasonably modest strength increase in the starting material to those that require larger increases.

The effective amounts of the various reactants combined according to the method of the present invention may vary depending, at least, on the amount of urease used, the characteristics of the permeable starting material and the conditions under which precipitation and/or cementation is to occur, the desired final strength, stiffness, or permeability of the treated porous material and the amounts of the other reactants in the reaction mix. The present application enables those of skill in the art to determine the relative amounts of the various reactants required for a given application and to apply the method to various starting materials and for a variety of end uses. The method of the present invention may be adapted to allow for the rate of mineral precipitation and/or cement formation to be controlled, as required. When rapid or slow formation of the precipitate or cement is desired the amounts and/or relative amounts of the reagents can be selected accordingly to bring about the desired rate of formation. In one non-limiting example, enhancement of the methods may comprise providing stronger nucleation sites on particles of the permeable starting material by high-pH pretreatment of the permeable starting material to be improved.

Depending on the requirements of a particular application or mode of use of the present invention, rapid formation of the precipitate and/or cement may be required. Alternatively it may be preferred for the precipitate or cement to be formed slowly. Based on the teachings herein, those of skill in the art will be able to modify the protocol to attain faster or slower formation of the precipitate and/or cement.

The methods of the invention may be performed a single time or may be repeated (once, twice, three times, or more) in order to attain the desired amount of cementation strength, stiffness increase, or permeability reduction. When the method is repeated to gain incremental increases in strength or stiffness or reduction in permeability, not all of the reagents need to be added each time. For example, residual urease activity may still be sufficient for one or more subsequent rounds of the method. A skilled person is readily able to determine the particular amounts of reagents required for use in subsequent rounds of the method of the present invention.

The methods may be applied in situ without disturbing the permeable starting material. This is particularly important for applications where the permeable starting material is delicate or fragile or for other reasons must not be disturbed. For example, when applied in the field where the soil to be improved (e.g. made resistant to earthquake-induced liquefaction) is underneath an existing structure or facility that is sensitive to ground movement (e.g. settlement or heave). As will be understood by those of skill in the art, the methods may comprise use of other components as appropriate for a given use. In one embodiment, the methods may further comprise use of an "organic additive." to increase enzyme stability, functional time and focus mineral precipitation. As used herein "organic additive" refers to a substance having reaction dependent biochemical properties such that the additive responds to changes in the chemical environment (i.e., ion concentration and ion type) by changing it properties (i.e., solubility, structural conformation, aggregation, and/or surface charge). The organic additives disclosed herein are water soluble and comprise protein stabilizing properties. In particular embodiments, the organic additive provides nucleation points in the permeable starting material. In some embodiments, the organic additive is powdered milk. In other embodiments, the organic additive is a colloid which is a homogeneous, noncrystalline substance consisting of large molecules or ultramicroscopic particles of one substance dispersed through a second substance. Colloids include gels, sols, and emulsions; the particles do not settle and cannot be separated out by ordinary filtering or centrifuging like those in a suspension), and hydrogels. In some embodiments the organic additive is present a concentration of about 4 g/L in a mixture comprising the isolated urease, urea and source of divalent cations. As used herein "about" includes concentrations within +/−5% of the recited concentration. In various further embodiments, the organic additive is present a concentration of 1-10 g/L. In various further embodiments the organic additive is present a concentration of 3-5 g/L. In various further embodiments the organic additive is present a concentration of 1 g/L, 2 g/L, 3 g/L, 5 g/L, 6 g/L or 7 g/L in a mixture comprising the isolated urease, urea and source of divalent cations. The methods of the present invention provide significant advantages over prior methods by providing significantly higher strengths at significantly lower carbonate content through focused mineral precipitation. This low carbonate content requires only one cycle of treatment, providing further benefits over previous treatment schemes for soil improvement, which typically require multiple cycles of treatment. The methods can be carried out under any temperature conditions suitable to promote carbonate cementation.

In a preferred embodiment, the permeable starting material comprises a column of the permeable starting material. As used herein, a "column" refers to relatively linear prisms of stiffened and/or strengthened soils used to reinforce the uncemented soil mass and/or transfer load to greater depths in the soil stratum. As will be understood by those of skill in the art, the prism of soil extends below a surface of the starting material. In various embodiments, the column is at least 0.5 meters long (deep) and 0.1 meters in diameter. In various further embodiments, the column is at least 1, 2, 3, 4, 5, 6, 7, 8, 9, 10, 15, 20, 25, 50, or more meters long/deep. In various further embodiments, the column is at least 0.2, 0.3, 0.4, 0.5, 0.6, 0.7, 0.8, 0.9, 1, 1.5, 2, 2.5, 3, 3.5, 4, 4.5, 5, 7.5, 10, or more meters in diameter. In this embodiment, the methods comprise combining the starting materials so that carbonate precipitation and/or cementation of the starting material occur at a desired location in the column. In one embodiment, carbonate precipitation and/or cementation occurs at only one or more specific areas within the column, such as at a specific location where the starting materials are combined within the column. In another embodiment, carbonate precipitation and/or cementation occur throughout the column.

This embodiment provides further improvements over prior methods, which are focused on improvement of the entire mass of soil in the improvement zone. In this embodiment, the methods permit production of stone-like materials via local cementation. Columns of improved starting materials, such as soils, have broad application in geotechnical practice, including improvement of foundation bearing capacity, support of embankments, slope stabilization, stabilization of the base of excavations, support of underground openings, and a variety of other geotechnical purposes. The limitations associated with bio-plugging can also be mitigated by using this technique to improve columns of soil (rather than the entire soil mass).

In one non-limiting example, consider a 4.2-meter long, 1-meter diameter column of soil with a porosity of 0.31 is to be improved by precipitating 5% calcium carbonate by weight. This column has a total volume of 3.29 m³ and a pore space of 1.0 m³. Assuming a calcium carbonate density of 2.71 g/cm³ (2710 kg/m³), approximately 136 kg of $CaCO_3$ is used to precipitate in the improvement zone (i.e. the column). To obtain 136 kg of $CaCO_3$ (1,360 moles), 81.6 kg of urea (1,360 moles) and 54.4 kg of calcium (1,360 moles) are used. Since there are 2 amine groups per urea molecule, 2,720 moles of ammonia nitrogen and 1,360 moles of carbon dioxide are released from 81.6 kg of urea. Assuming a minimum urease activity of 15,000 units/gram urease powder (type 3 urease from Jack bean [Sigma Aldrich]), where one-unit is the release of 1.0 mg ammonia nitrogen from urea in 5 minutes at pH 7.0 at 20° C., then 10 grams of this particular grade of enzyme (150,000 units) will release 150 grams of ammonia nitrogen 0.8 moles) in 5 minutes. Therefore, 26 hours (1546 minutes) are required to fully catalyze the release of carbon dioxide and ammonia from 81.6 kg of urea.

In a second aspect, the present invention provides kits comprising
(a) isolated urease;
(b) urea;
(c) a source of divalent cations, preferably calcium ions; and
(d) an organic additive
wherein (a), (b), (c), and (d) are provided in amounts effective to cause carbonate cementation when combined with a permeable starting material.

All definitions, embodiments, and combinations thereof of the first aspect apply equally to this second embodiment, unless the context clearly dictates otherwise. Thus, the kits may further contain any of the components or combinations thereof disclosed for use with the methods of the invention, including but not limited to stabilizers, buffers, nucleation aids, etc.

The use of plant-derived urease enzyme offers many benefits over the use of microbially-generated urease to induce carbonate cementation for soil improvement, a process that has garnered much attention recently. In this biogeochemical soil improvement process, urea hydrolysis is catalyzed by the urease enzyme (urea amidohydrolase), a widely occurring protein found in many microorganisms, higher order plants, and some invertebrates, to precipitate calcium carbonate in the presence of calcium. The calcium carbonate precipitate ($CaCO_3$) forms cementation bonds at inter-particle contacts and also fills the void space in granular soils. Urease is a nickel-dependent, metalloenzyme that is approximately 12 nm by 12 nm (subunit). By comparison, nearly all known bacteria that generate urease are greater than 300 nm in diameter, with the majority in the range of 500-5000 nm. As soil improvement by ureolytic carbonate precipitation requires penetration of the pore spaces by the improvement media, the small size of the enzyme affords the use of plant-derived enzyme a distinct advantage over microbial methods, including the ability to penetrate finer grained soils and less sensitivity to bioplugging (clogging of the pore space by the precipitate). An additional benefit of the use of plant-derived enzyme compared to microbially-derived enzyme is that the 100% of the carbon in the substrate is available for conversion to $CaCO_3$. Furthermore, plant derived enzyme is widely available.

EXAMPLES

Example 1

Carbonate Cementation Via Plant Derived Urease

Methods
Ottawa 20-30 Sand

Laboratory column tests were conducted using plant derived urease to induce $CaCO_3$ precipitation in Ottawa 20-30 sand These tests were carried out in 6"×2" (152 mm×51 mm) acrylic tubes and membrane-lined 2.8"×6" (71 mm×152 mm) split molds (for creating specimens for triaxial testing). Three acrylic tubes and two columns for triaxial testing were filled with 20-30 Ottawa silica sand (mean grain size 0.6 mm, coefficient of uniformity 1.1) and treated as follows: tube #1: the sand was dry pluviated via funnel at ≈3" (76 mm) drop height and then received 5 applications of a cementation solution containing urea and calcium chloride mixed with 1.4 g/L enzyme (total solution volume≈300 ml); tube #2: sand was added in same manner as tube #1 and then received 2 applications (≈150 ml total) of the same cementation solution mixed with 1.4 g/L enzyme; tube #3: the lower-third of tube was filled with sand and dry enzyme (≈3 g), the remainder of the tube contained dry pluviated sand without enzyme, and the tube then received 2 applications (≈150 ml) of the cementation fluid with no enzyme added.

Approximately 100 mL of a pH=7.8 solution containing 383 mM urea (reagent grade, Sigma-Aldrich), 272 mM $CaCl_2$-$2H_2O$ (laboratory grade, Alfa Aesar) was used for the first application in each acrylic tube. Subsequent applications employed approximately 50 mL of a pH=7.6 solution containing 416 mM urea and 289 mM $CaCl_2$-$2H_2O$. Solution concentrations, while variable, were formulated within a reasonably similar range as a matter of convenience. In each application, the cementation fluid was poured into the top of the acrylic tube with the bottom closed off. The cementation fluid was allowed to stand, loosely covered, in the acrylic tube for at least 24 hours and then drained out the bottom of the cylinder. The next application followed immediately after drainage was complete. Drainage was accomplished by puncturing the base of the cylinder with a 20-gauge needle. When drainage was complete, the needle was removed and the puncture was plugged with a dab of silicone. Occasionally, the needle became plugged and an additional needle was inserted through the base. The triaxial columns were filled with sand in the same manner as tube 1 and then received 2 applications (each application≈250 ml) of cementation solution with 1.4 g/L enzyme.

In each application of cementation fluid, the fluid was added until it rose to approximately ½-inch (12-mm) above the soil line. After 2 applications, tubes #2 and #3 were allowed to air dry for several days and then analyzed. Experimentation with tube #1 was continued for several more days as three more batches of cementation fluid were applied. The last 2 applications of cementation fluid were allowed to slowly drain through the needle in the base immediately after application rather than sit for 24 hours (drainage rate≈10-25 ml/hour). The triaxial columns were allowed to stand for at least a week after the second cementation fluid application and then drained.

After drainage was complete, the triaxial columns were moved to a triaxial testing device. After draining the specimens from the acrylic tubes and after the completion of the triaxial tests, all samples were triple washed with de-ionized water. Tubes #2 and #3 were separated in 3 layers, while tube #1 was separated into six layers (for better resolution). Each layer from the specimens in the acrylic tubes and the entire mass of the triaxial specimens were acid washed to determine $CaCO_3$ content by oven drying for 48 hours, weighing, digesting with warm 1M HCl, washing, drying, and reweighing to determine carbonate mineral content.

Several of the cemented specimens were analyzed for mineral identification using X-Ray Diffraction (XRD). Samples were ground in an agate mortar and pestle and powdered onto a standard glass slide for analysis. Scanning electron microscopy (SEM) imaging was performed on intact cemented chunks of material with an Agilent 8500 Low-Voltage SEM (LV-SEM). A LV-SEM is a field emission scanning electron microscope capable of imaging insulating materials, such as organic and biological substances without the need for a metal coating and without causing radiation damage to samples.

Ottawa F-60 Sand

A triaxial column was prepared using Ottawa F-60 silica sand (mean grain size 0.275 mm, coefficient of uniformity 1.74) to investigate enzymatic ureolytic $CaCO_3$ precipitation in a finer grained material. The specimen was prepared in the same manner as described for the triaxial columns for the Ottawa 20-30 sand. The cementation fluid for the first of the two applications contained approximately 2.0 g/L enzyme, 400 mM urea (reagent grade, Sigma-Aldrich), 300 mM $CaCl_2$-$2H_2O$ (laboratory grade, BDH) at pH=7.7. The fluid for the second application contained 1 M urea-$CaCl_2$-$2H_2O$ solution at pH=7.8 without any enzyme. After the test, the triaxial specimen was washed and subject to acid digestion in the same manner as the Ottawa 20-30 triaxial specimens.

Results

Acrylic Tubes

Approximately 100 ml of cementation solution was delivered per application for the first application in each acrylic tube. However, the amount of solution the tube would accept was notably reduced in subsequent applications, when less than 75 ml was typically required to fill the tubes to ≈½ inch (12 mm) above soil line. At the conclusion of the experiment, precipitation was visible along the entire length of tubes 1 and 2. Internally the cementation was variable, with some highly cemented zones and other zones with little to no cementation.

Tube 1 yielded mostly small, loose chunks of sand with strong effervescence upon digestion. Most of this column appeared un-cemented and exhibited unusually viscous behavior when wet. A fairly large (compared to column diameter) piece of strongly cemented sand (not breakable without tools) formed in the deepest layer of tube 1. Tube 2 had many small chunks of weakly cemented sand with strong effervescence upon digestion. Tube 3 had little to no precipitation in the top layer (i.e. this layer did not show any indication of carbonate upon acid digestion.) The deepest layer of tube 3 contained many pieces of weakly cemented sand that effervesced strongly upon digestion. The middle layer of tube 3 contained a few pieces of cemented sand that effervesced moderately upon digestion. The results from the acid washing are presented in Table 1.

TABLE 1

Results from Experiment Set 1 using 20-30 Ottawa silica sand Summary of Results

| Tube # | Layer | Weight Change via Digestion | Amt. of $CaCO_3$ (g) | Total Amt. $CaCO_3$ (g) | Theor. Max $CaCO_3$ (g) |
|---|---|---|---|---|---|
| 1 | 1 | 11% | 3.57 | 11.8 | ≈14.5 |
|   | 2 | 3.8% | 1.67 |   |   |
|   | 3 | 2.7% | 1.73 |   |   |
|   | 4 | 2.1% | 1.40 |   |   |
|   | 5 | 2.3% | 1.74 |   |   |
|   | 6 | 2.0% | 1.64 |   |   |
| 2 | 1 | 0.76% | 0.63 | 2.07 | ≈4.35 |
|   | 2 | 0.65% | 0.69 |   |   |
|   | 3 | 0.49% | 0.75 |   |   |
| 3 | 1 | 0.23% | 0.31 | 3.57 | ≈4.35 |
|   | 2 | 0.58% | 0.63 |   |   |
|   | 3 | 1.7% | 2.63 |   |   |

The theoretical maximum $CaCO_3$ content is the stoichiometric maximum balanced on initial concentrations. The primary experimental differences between the tests are (1) the number of applications of cementation fluid and (2) the manner in which the urease was delivered. The results indicate that there is greater carbonate precipitation with increasing number of applications, as expected. The data show more precipitation in (or on) the top layer of tubes 1 and 2 but not in tube 3, as the enzyme was physically confined to the lower-third layer in tube 3 during sample preparation. In the top layer of tube 3, where no urease was mixed with the sand, carbonate precipitation was nearly undetectable. There was no visual evidence of precipitation and practically no measurable change in weight of this layer after acidification (weight change=0.23%). In the bottom layer of tube 3, where 3 g of dry enzyme was mixed with the soil, there was a weight change of 1.7% following acid washing. The middle layer of this specimen had a minor change in weight (0.58%), possibly due to uneven distribution of the layers during preparation or splitting of the specimen or to upward migration of urease from the bottom layer.

XRD analysis confirms that calcite is the mineral phase present in the cemented soil chunks. LV-SEM images, presented in FIG. 1, show silica (quartz) sand particles cemented with calcium carbonate and various morphological features associated with the cementation process on the silica surface.

Triaxial Columns

Figure 2:
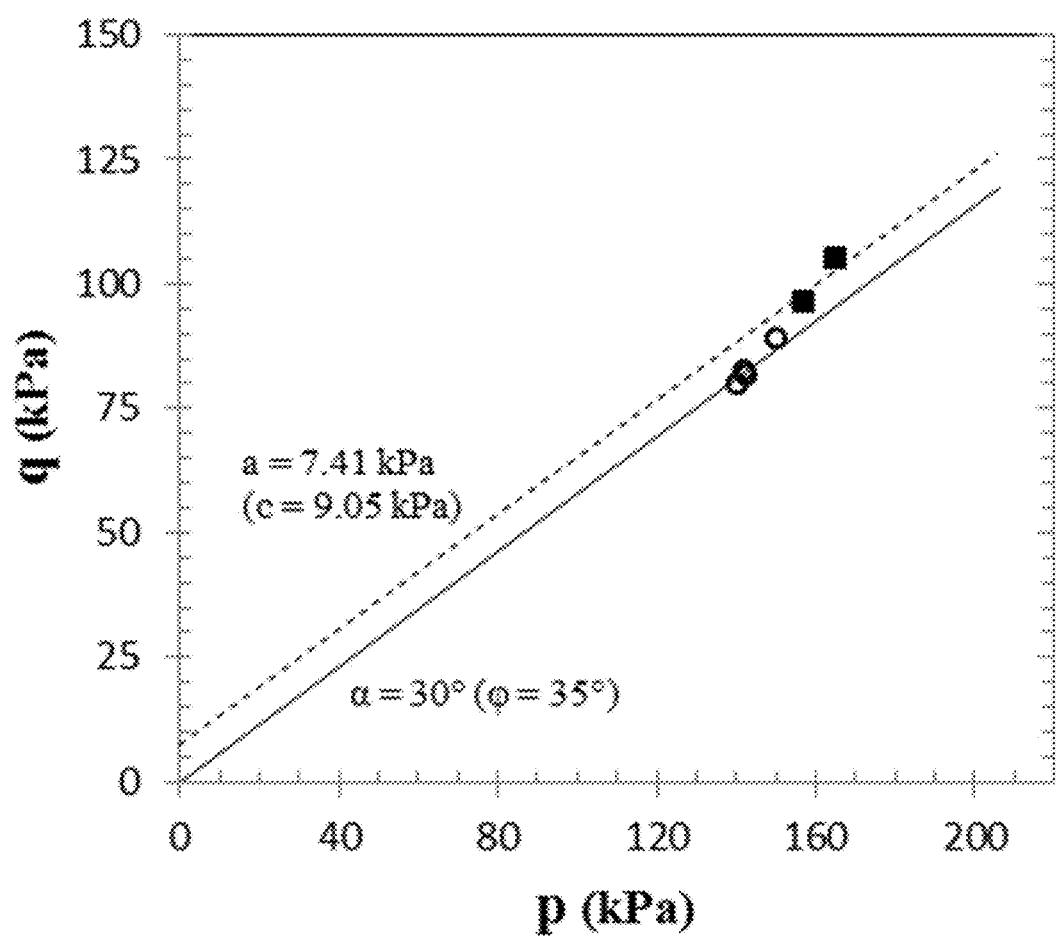
FIG. 2. P-q plot failure envelopes for 20-30 silica sand: ■Cemented ($D_r$=60%); ○ Uncemented ($D_r$=60%)
Figure 3:
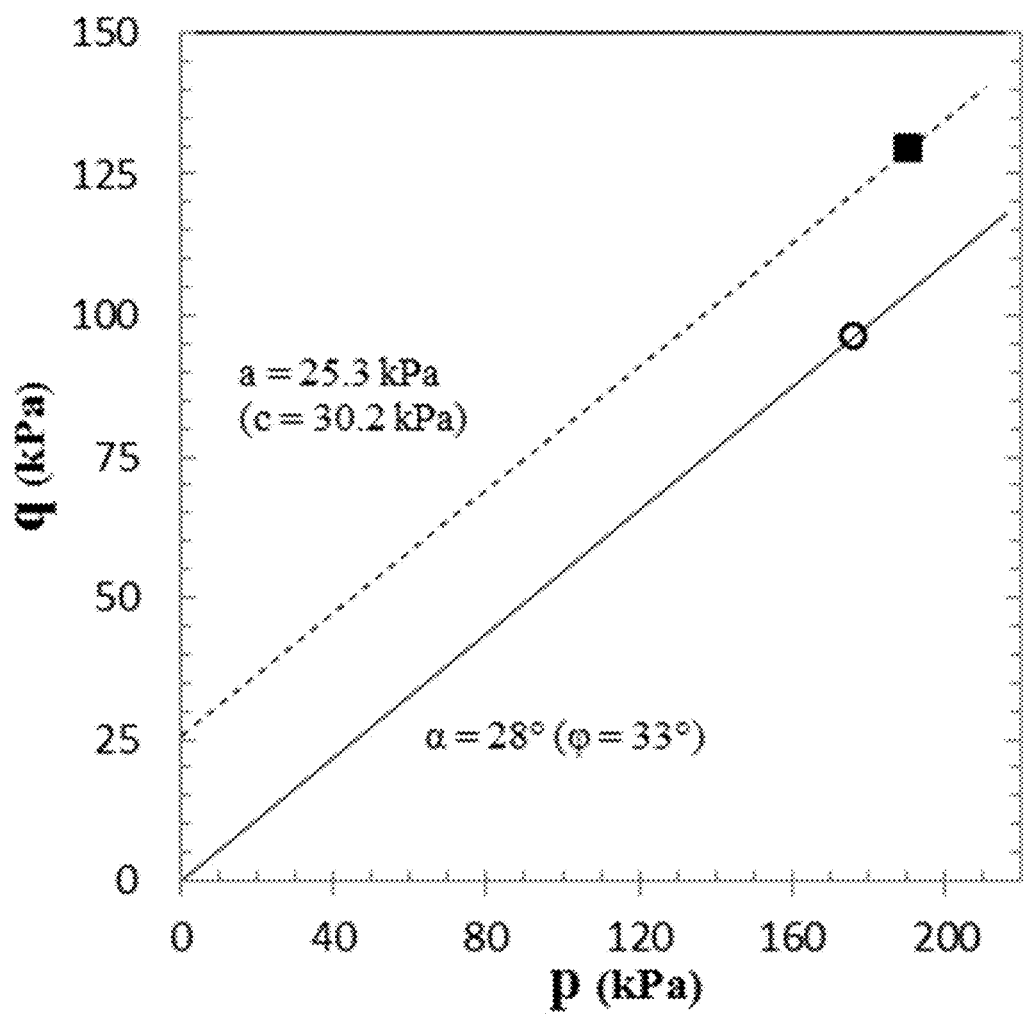
FIG. 3. P-q plot failure envelopes for F-60 silica sand: ■Cemented ($D_r$=3 5%); ○ Uncemented ($D_r$=37%)

The three triaxial sand columns (2 Ottawa 20-30 sand columns and 1 Ottawa F-60 sand column) were tested in drained triaxial compression prior to acid digestion. All three columns were able to stand upright after removal of the split mold. The results of the triaxial compression tests performed on the 20-30 Ottawa sand are presented in FIG. 2 and the results for the F-60 Ottawa sand are presented in FIG. 3. The carbonate cement content for one of the 20-30 silica sand columns was 2.0% $CaCO_3$ (by weight). The carbonate content of the other 20-30 Ottawa sand column could not be quantified due to unintended sample loss. The carbonate cement content for the finer grained F-60 Ottawa sand was 1.6% $CaCO_3$ (by weight). The results show substantial strength increase for all 3 sand columns tested.

Conclusion

Sand column tests have shown that agriculturally-derived urease can be used to induce calcium carbonate precipitation in sand. Sand columns were developed using Ottawa 20-30 and F-60 sand and three different preparation methods: dry pluviation followed by percolation of a calcium-urease-urea cementation solution, pluviation into a calcium-urease-urea cementation solution, and mixing the sand with urease prior to pluviation with a calcium-urea solution. Cementation was observed in all of the columns. XRD and SEM testing confirmed that calcium carbonate (specifically calcite) was the cementing agent. Acid digestion showed that increased applications yielded correspondingly greater carbonate precipitation. The quality of cementation, as determined by the effort needed to break apart cemented chunks of sand, varied depending on the sampling location within the column. Triaxial test results on cemented columns showed substantial strength increase over non-cemented columns at the same relative density.

Example 2

Enzyme Induced Carbonate Precipitation with a Powdered Milk Organic Additive

Methods

EICP Treatment Solutions

EICP solutions were prepared by dissolving EICP constituents in deionized water with an organic additive (test) and without the organic additive (control). The experiments employed two different concentrations of the substrate (urea) and enzyme in the organic additive-enhanced solution: one a relatively low concentration (0.37 M urea, 0.25 M $CaCl_2$, 0.8 g/l urease) and one a relatively high concentration (1 M urea, 0.67 M $CaCl_2$, 3.0 g/l urease). Only the solution with the higher concentrations was used for the control specimens. Reagent grade (≥99% purity) urea and calcium chloride in the form of $CaCl_2$-$2H_2O$ were used, and the enzyme used was jack bean urease from Fisher Scientific. Concentrations of constituents used in the tests were:

Solution 1: 1 M of urea, 0.67 M of $CaCl_2$, and 3 g/l of urease enzyme without organic additive.

Solution 2: 1 M of urea, 0.67 M of $CaCl_2$, 3 g/l of urease enzyme, and 4 g/l powdered milk organic additive.

Solution 3: 0.37 M of urea, 0.25 M of $CaCl_2$, 0.8 g/l of urease enzyme, and 4 g/l powdered milk organic additive.

Sample Preparation

Soil columns were prepared in acrylic cylinders that were filled with Ottawa 20-30 sand (US Silica Company), a uniform quartz sand with a mean grain size of 0.6 mm, to investigate enzymatic ureolytic $CaCO_3$ precipitation. The acrylic cylinders measured 101.6 mm high and 50.8 mm in inner diameter (4"×2"). A polypropylene (PP) liner was placed inside of the acrylic columns to ease sample extraction for UCS testing. The bottoms of the columns were closed with rubber caps and sealed with silicone glue to minimize leakage. The PP liner extended above the acrylic cylinder and its top was loosely closed to minimize evaporation of the EICP solution. Each soil column was prepared by first pouring 75 ml of the EICP solution (corresponding to slightly more than one pore volume of the final specimen) into a bowl containing 350 g of 20-30 Ottawa sand and then thoroughly mixing the sand and solution. The sand-EICP solution mixture was then quickly placed into the acrylic column in three layers. Each layer was compacted by tamping 25 times with a small hammer to reach a relative density of 90% (based upon the dry weight of soil). The hammer weighed 11.56 N (2.6 lb.). After compaction, the solution was always a few millimeters above the soil, indicating that the soil is under an inundated (almost saturated) condition.

Sample Curing

The compacted soil and cementation fluid was allowed to stand in the acrylic cylinders for at least 72 hours at room temperature. Any fluid remaining in the columns was then drained out from the bottom of the cylinder, followed by an 80 ml of DI water rinse (slightly more than one-pore volume) that was added slowly to the top of each column to flush out any remaining EICP solution and soluble salts. After draining and flushing were complete, each treated specimen was extracted from the acrylic cylinder. Then, selected samples were soaked in DI water for at least one half hour (as described subsequently). All samples were placed into an oven at (40° C.) until a constant mass was achieved. Once oven drying was complete, specimens were prepared for the UCS Test.

Unconfined Compressive Strength Testing (UCS Testing)

UCS testing was conducted in according with ASTM D4918. Prior to performing the UCS test, the top and bottom surface of each sample was leveled using plastic steel putty from ITW Devcon.

Triaxial Testing

Undrained triaxial tests were conducted on samples prepared using Solution 2 in order to measure the shear strength of the treated soil. In these tests, the Ottawa 20-30 sand was prepared at a relative density of 40%, instead of 90% for comparison to results of specimens compacted to 40% relative density and treated using microbially induced carbonate preparation (MICP). The samples were prepared by pouring the dry soil through a funnel (air pluviation of dry soil). Before applying the confining pressure, each sample was back pressure saturated until Skempton's B parameter was above 0.95. Samples were tested at confining pressures of 50 kPa, 100 kPa, and 150 kPa. Each test was performed at a constant axial strain rate of 0.5% per minute to a final strain of 20%.

Acid Digestion

Following UCS and triaxial testing, intact pieces of samples were dried in an oven at 105° C. for 24 hours, weighed, and then washed with a strong (4 M) hydrochloric acid (HCl) solution to determine the mass of calcium carbonate precipitates. Following treatment with HCl, the samples were rinsed with deionized (DI) water and dried in the oven at 105° C. The mass difference before and after the acid-wash was considered as the mass of the carbonates precipitated in the specimen.

Micro Scale Identification Analysis

X-Ray Diffraction (XRD) analysis was performed on intact pieces of selected specimens to identify mineral crystal phases existing in each sample. The samples were ground using an agate mortar and pestle and powdered onto a standard glass slide for XRD analysis. Scanning electron microscopy (SEM) imaging was also performed on intact cemented chunks of material. Energy dispersive X-ray (EDX) analysis was also carried out in conjunction with SEM imaging to determine the elemental composition of each sample. The samples were coated with carbon prior to SEM/EDX analysis.

Results

Tests Using EICP Solution 1

Two columns were prepared using EICP Solution 1, i.e., composed of 1 M urea, 0.67 M $CaCl_2$, and 3 g/L of urease enzyme without organic additive. The results of UCS testing and acid digestion on these two specimens are shown in Table 2.

TABLE 2

Results of UCS and Carbonate Precipitation Using Solution 1

| Column | $CaCO_3$ (%) | Peak Strength (kPa) |
|---|---|---|
| 5-1 | 1.63 | 133 |
| 5-2 | 0.98 | 158 |

Figure 4:
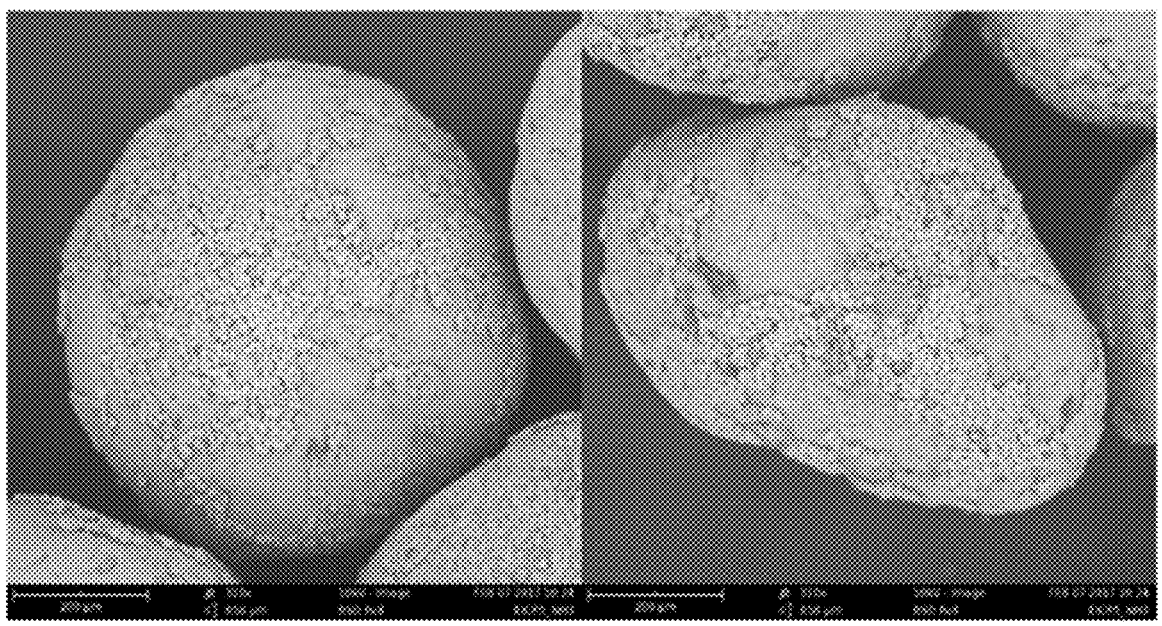
FIG. 4. Scanning electron microscope (SEM) images of samples treated using 1 M of urea, 0.67 M of $CaCl_2$, and 3 g/l of urease enzyme without organic additive (solution 1).

SEM images were taken of these samples to provide visual evidence of $CaCO_3$ precipitation. The image in FIG. 4 shows that the calcium carbonate precipitate was spread around the surface of the sand particle.

Tests Using EICP Solution 2

A series of specimens were prepared using EICP Solution 2, a solution containing 1 M of urea, 0.67 M of $CaCl_2$, 3 g/l of urease enzyme, and 4 g/l of powdered milk organic additive; this solution was the same as Solution 1 except with the addition of organic additive. UCS testing of specimens treated with Solution 2 yielded significantly higher strength than those prepared with Solution 1 (i.e., by a factor between 6 and 20) at similar carbonate content. The UCS and carbonate content of the tests using Solution 2 are presented in Table 3.

TABLE 3

Strength and percentage of precipitation mass for samples treated with Solution 2
1M Urea, 0.67M $CaCl_2$, 3 g/L of urease, 4 g/L powdered milk

| Column | Peak Strength (kPa) | $CaCO_3$ (%) | Rinsed or Soaked |
|---|---|---|---|
| 5-3 | 911 | 1.02 | Soaked Overnight |
| 5-4 | 1817 | 0.82 | Rinsed in Column |
| 5-5 | 1010 | 0.78 | Rinsed in Column |
| 5-6 | 463* | 0.84 | Rinsed in Column |
| 5-7 | 1654 | 0.79 | Rinsed in Column |
| 5-8 | 1763 | 1.17 | Rinsed in Column |

*Cap failed, so tested just the bottom of the column

Figure 5:
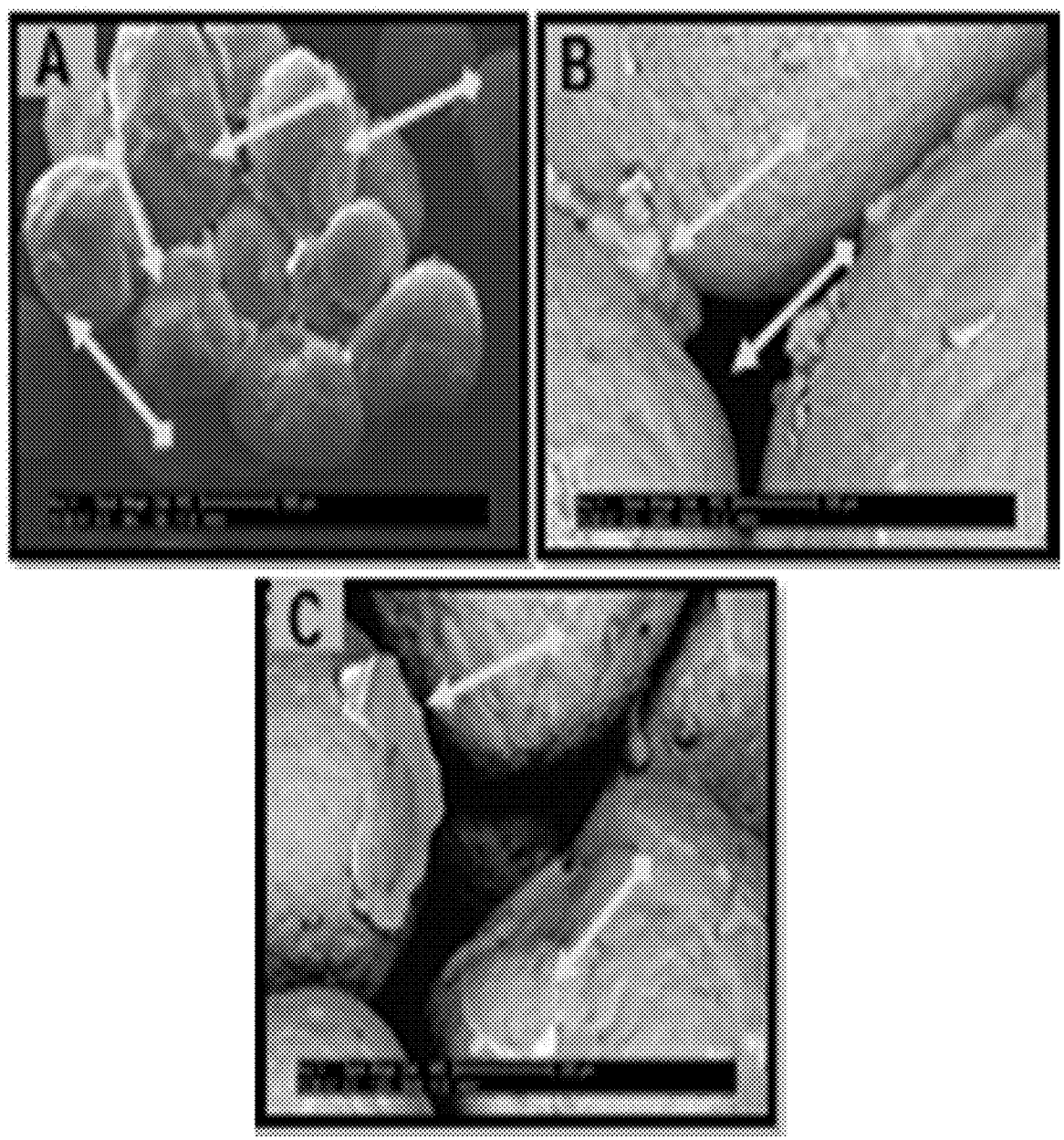
FIG. 5. SEM images using 1 M of urea, 0.67 M of $CaCl_2$, 3 g/l of urease enzyme, and 4 g/l organic additive (solution 2): (A) $CaCO_3$ at inter-particle contact points, (B) Inter-particle cementation, (C) Broken $CaCO_3$ at inter-particle contact.
Figure 6:
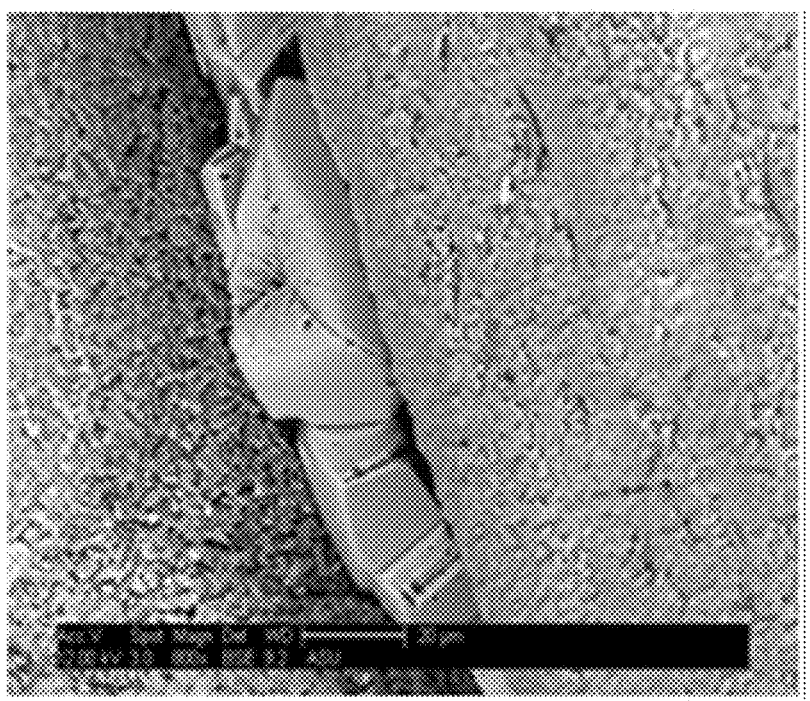
FIG. 6. Rhombohedral calcite crystals at inter-particle contact points (A). The results of energy dispersive x-ray spectroscopy (EDX) analysis confirm the presence of the elements constituting calcium carbonate and silica (B).
Figure 6:
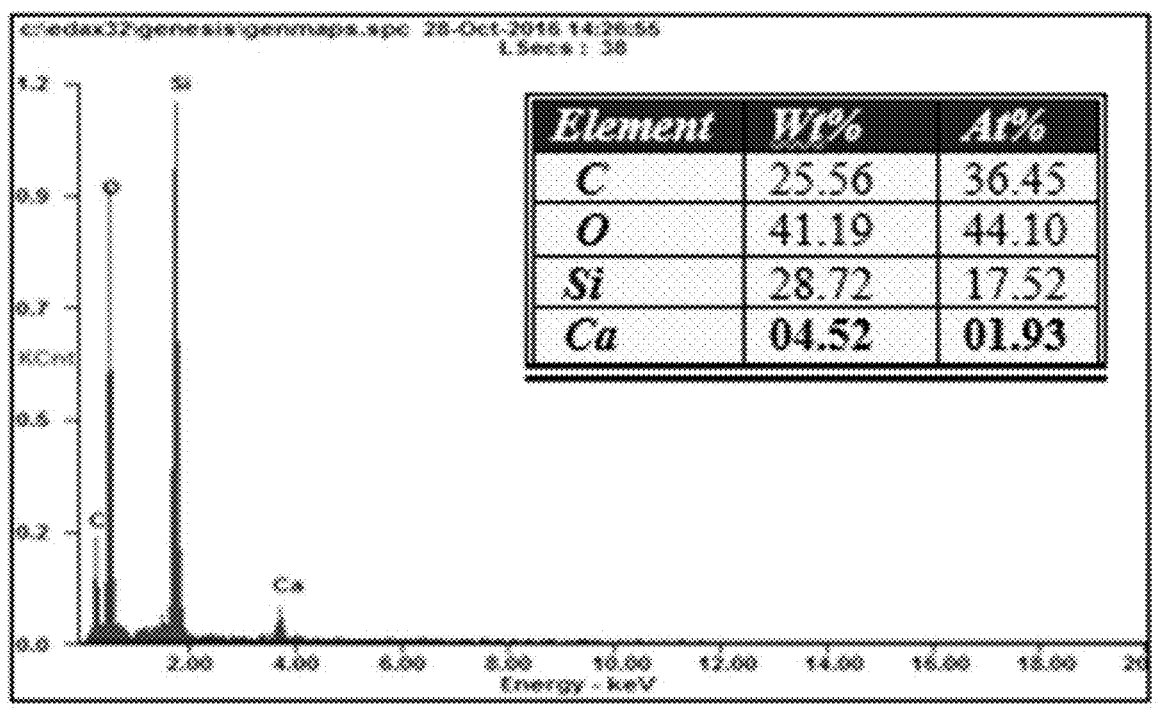
Figure 7:
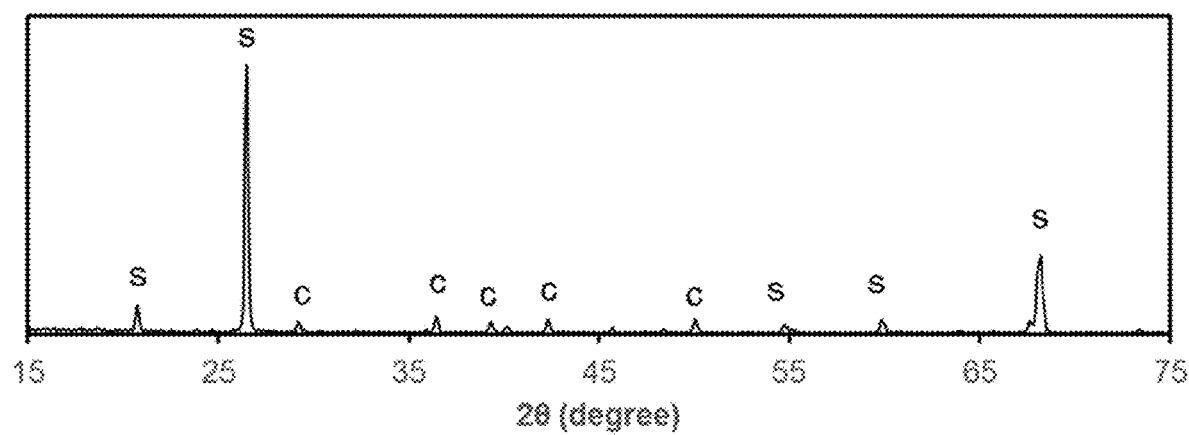
FIG. 7. X-Ray diffraction (XRD) spectrum from powdered XRD analysis showing the corresponding peaks of calcite crystal phase and silica sand. (S: silica sand and C: the calcite).

Scanning electron microscope (SEM) images of specimens prepared using Solution 2 are presented in FIG. 5. These images exhibit a pattern of precipitation that may be characterized as densely agglomerated calcite crystals at inter-particle contact points. FIG. 6 presents the results of EDX analysis focused at the contact point of a specimen treated using Solution 2. The EDX analysis yields a carbonate percentage of around 2%, higher than measured for the bulk sample (as expected), but still significantly lower than reported by others for the same UCS. The results from XRD analysis presented in FIG. 6 demonstrate that the precipitate is primarily calcite.

Tests Using EICP Solution 3

Two samples were treated using Solution 3, a solution with a lower concentration of constituents than Solution 2. Solution 3 contained 0.375 M urea, 0.25 M $CaCl_2$, 0.8 g/L enzyme, and 4 g/L of powdered milk organic additive (37.5% of the urea and calcium in the other solutions). The results of the tests on these specimens, shown in Table 4, still yield a strength of over 1 MPa at very low $CaCO_3$ content. Furthermore, the amount of $CaCO_3$ precipitated was around the theoretical maximum.

TABLE 4

Results of UCS and Carbonate Precipitation Using Solution 3
0.375M Urea, 0.25M CaCl2, 0.85 g/L of urease, 4 g/L powdered milk

| Column | Peak Strength (kPa) | $CaCO_3$ % | Rinsed or Soaked |
|---|---|---|---|
| 5-26 | 1000 | 0.57 | Soaked overnight |
| 5-27 | 1396 | 0.71 | Rinsed in Column |

Figure 8:
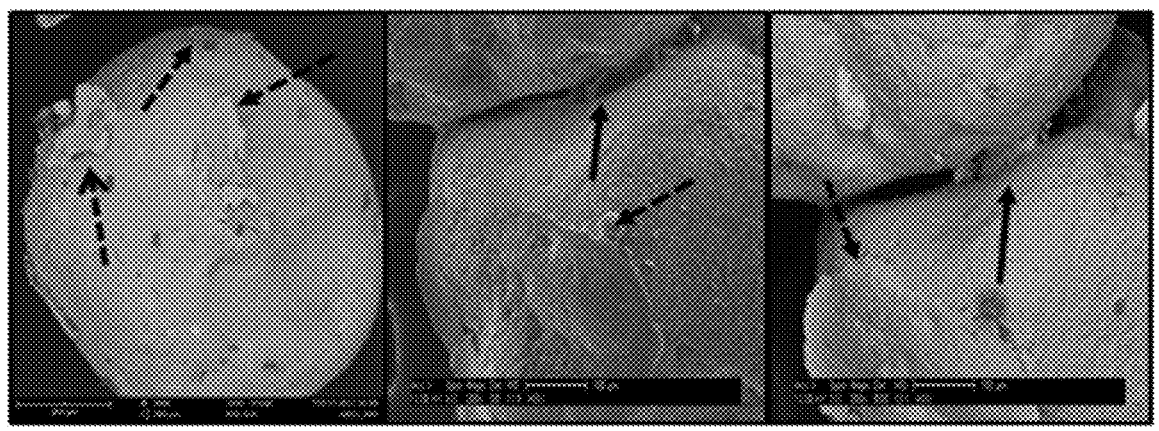
FIG. 8. SEM images using 0.37 M of urea, 0.25 M of $CaCl_2$, 0.8 g/l of urease enzyme, and 4 g/l organic additive (solution 3), showing the $CaCO_3$ cementation at inter-particle contact points (solid-arrow), and broken $CaCO_3$ at inter-particle contact (dotted line).

SEM images of the specimens prepared using Solution 3, the lower concentration of urea, $CaCl_2$, and urease enzyme, are shown in FIG. 8. These images shows the same pattern of concentrated precipitation at inter-particle contacts than seen when the higher concentration of urea, $CaCl_2$, and urease enzyme was used with organic additive.

Comparison to Previous EICP Test Results

Figure 9:
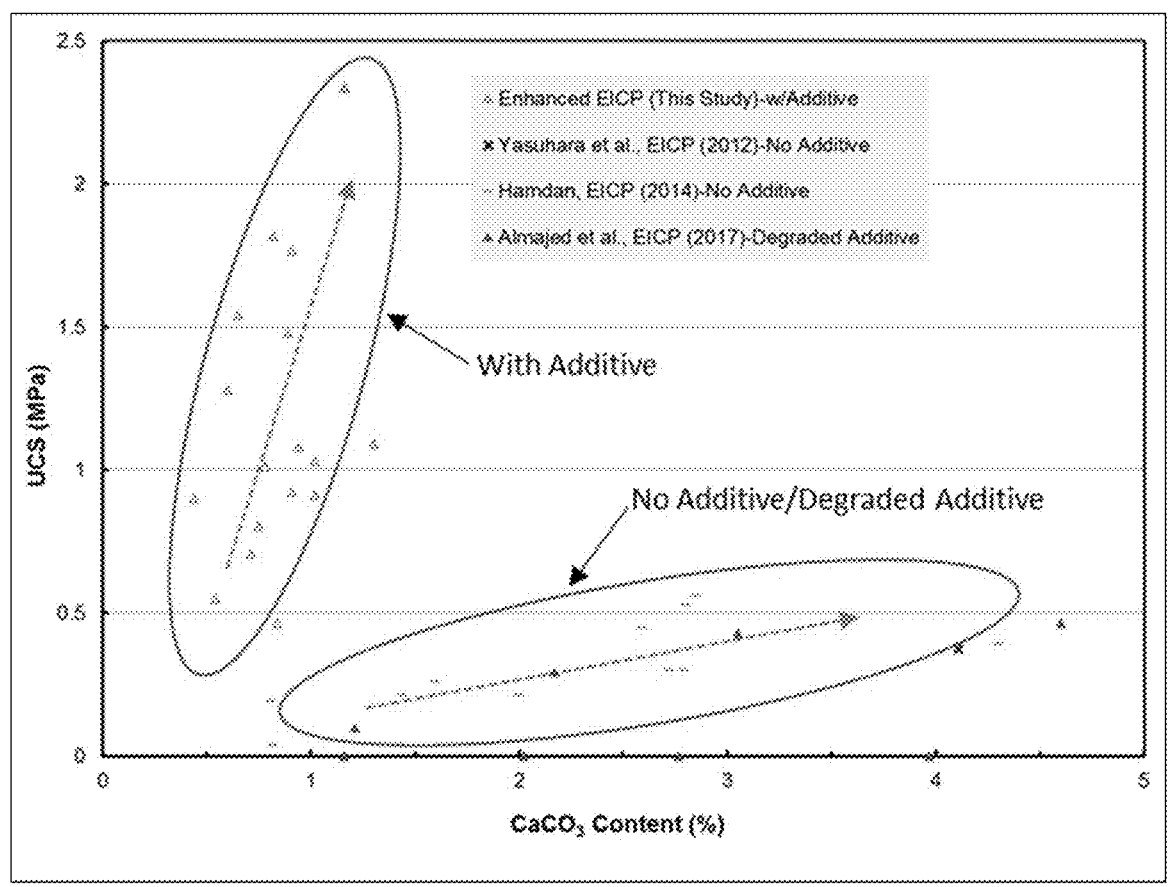
FIG. 9. Strength and $CaCO_3$ values limited to 2.5 MPa and 5% (respectively) to further illustrate unexpectedly high strength values at very low $CaCO_3$ contents when using the powdered milk organic additive (open triangles) compared to enzyme-induced carbonate precipitation (EICP) without the additive or with a degraded form of the additive. Trend lines added to illustrate strength values of EICP when using the organic additive (open triangles) compared to EICP without the additive or with a degraded form of the additive (all other symbols).

FIG. 9 compares the results of UCS tests on soil improved using EICP reported by others in the literature to the results reported herein. Previous testing reported in the literature by Yasuhara at al., *Soils and Foundations* (2012), 52(3):539-49, the only other group to report in the literature on strength testing of EICP-improved soil, yield strengths on the order of 100 KPa (0.1 MPa) at carbonate content of around 1 percent and a strength of around 400 KPa at carbonate content of around 4.6%. Previous testing using the control EICP solution conducted by Hamdan (2015), "Applications of Enzyme Induced Carbonate Precipitation (EICP) for Soil Improvement," Doctoral Dissertation, Arizona State University, and by Almajed et. al (2017) "Enzyme Induced Carbonate Precipitation (EICP) for Soil Improvement," Doctoral Dissertation, Arizona State University, using a degraded organic additive-enhanced EICP solution (a solution prepared using expired powdered milk) provided results similar to those reported by Yasuhara at al., *Soils and Foundations* (2012), 52(3):539-49. As shown in FIG. 9, the tests conducted using the fresh organic additive surprisingly yielded significantly higher strength at lower carbonate content and with just one cycle of treatment.

Comparison to Previous MICP Test Results

Figure 10:
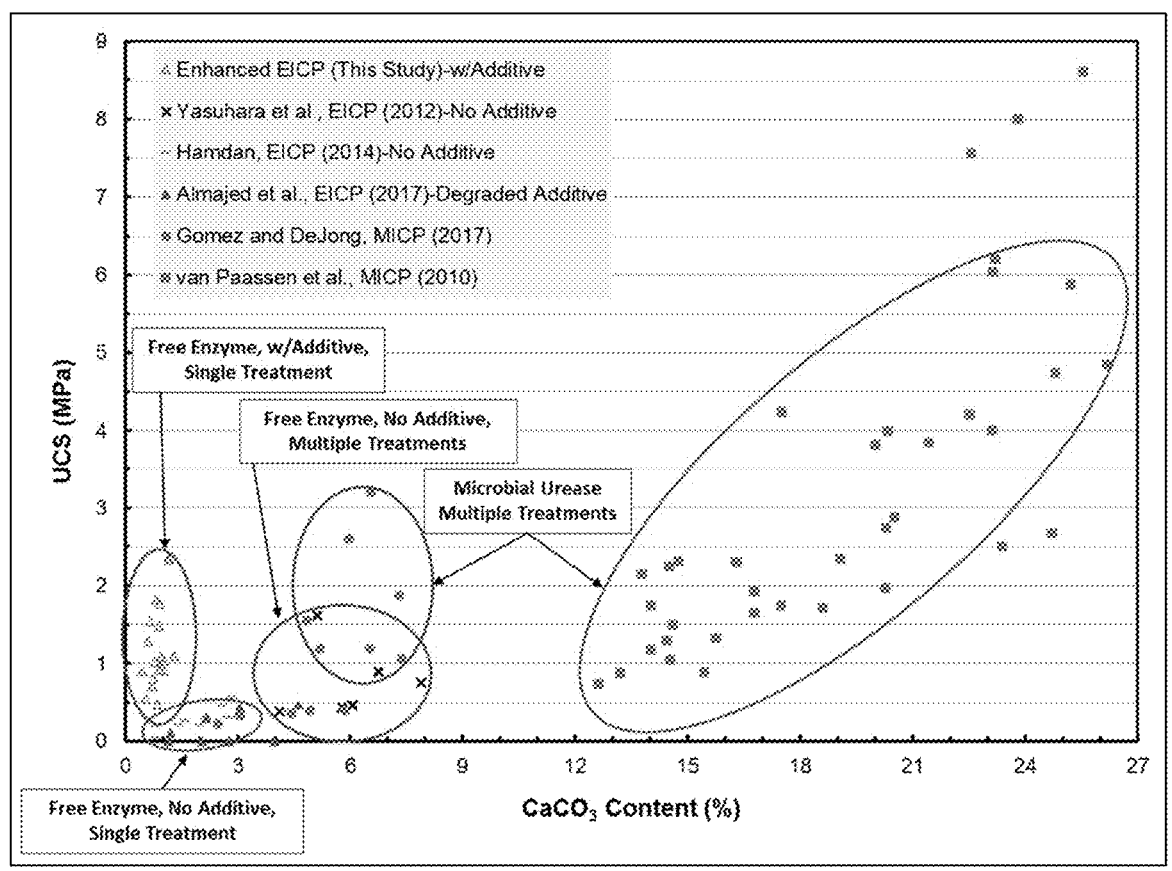
FIG. 10. Soil strength vs. calcium carbonate ($CaCO_3$) content. Comparison of EICP and microbially-induced carbonate precipitation (MICP) from various studies. UCS=unconfined compressive strength. MICP is microbially mediated process, whereas EICP is an enzyme (non-living) catalyzed reaction.

FIG. 10 compares the UCS test results reported herein to both the tests on EICP-improved soil conducted by others (those reported above and additional testing conducted by Gomez and Dejong, "Engineering Properties of Bio-cementation Improved Sandy Soil," *Conference Proc. from Grouting* 2017, (2017), 23-33 and van Paassen et al., "Quantifying Biomediated Ground Improvement by Ureolysis: Large-Scale Biogrout Experiment," *J. Geotechical & Geoenvironmental Engineering* (2010): 1721-28) using multiple treatment cycles and the results of tests on soil improved by MICP. It can be seen that the tests conducted using the organic additive-enhanced EICP solution yield significantly higher strengths at low carbonate content (carbonate content less than 1.5% and that multiple cycles of treatment and a significantly higher carbonate content (greater than 12%) was required to achieve strengths comparable to those achieved with the enhanced EICP solution.

We claim:

1. A cementation method, comprising combining a column of a permeable starting material or a column of a non-porous but fractured starting material with a mixture comprising:
   (a) isolated urease;
   (b) urea;
   (c) a source of divalent cations; and
   (d) an organic additive,
   wherein (a), (b), (c) and (d) are provided in amounts effective and the combining is carried out under conditions suitable to cause carbonate precipitation and/or cementation of the starting material within the column, and
   wherein the combining comprises:
   (i) mixing the urease with the starting material; and
   (ii) injecting into the column of starting material, under pressure and via an injection tube, a solution comprising the urea and the source of divalent cations.

2. The method of claim 1, wherein the method is used for one or more of improving bearing capacity of foundations; reducing settlement potential of foundations or embankments; increasing lateral resistance of foundations; enhancing stability of slopes or embankments; or reducing lateral earth pressures on retaining walls.

3. The method of claim 1 wherein the starting material comprises at least one of sand, silt, soil, clay, sediments, sawdust, fractured crystalline rocks, cracked concrete or sedimentary rocks.

4. The method of claim 1, wherein the isolated urease comprises jack bean urease.

5. The method of claim 1, wherein the source of divalent cations comprises a source of divalent calcium ions.

6. The method of claim 1, wherein the combining step is carried out more than once.

7. The method of claim 1, wherein the combining step is carried out once.

8. The method of claim 1, wherein the permeable starting material comprises sand.

9. The method of claim 1 wherein the injecting is carried out two or more times.

10. The method of claim 1 wherein the urease is mixed with starting material in only a portion of the column prior to the injecting step.

11. The method of claim 1, wherein the organic additive is water soluble.

12. The method of claim 1, wherein the organic additive is powdered milk.

13. The method of claim 1, wherein the organic additive is present in the mixture at a concentration of 1-10 g/L.

14. The method of claim 13, wherein the organic additive is present in the mixture at a concentration of 3-5 g/L.

15. The method of claim 13, wherein the organic additive is present in the mixture at a concentration of about 4 g/L.

* * * * *